(12) United States Patent
Chu et al.

(10) Patent No.: US 11,280,786 B2
(45) Date of Patent: *Mar. 22, 2022

(54) METHOD FOR FORMING BIOCHIPS AND BIOCHIPS WITH NON-ORGANIC LANDINGS FOR IMPROVED THERMAL BUDGET

(71) Applicant: Taiwan Semiconductor Manufacturing Company, Ltd., Hsinchu (TW)

(72) Inventors: Chia-Hua Chu, Zhubei (TW); Allen Timothy Chang, Hsinchu (TW); Ching-Ray Chen, Taipei (TW); Yi-Hsien Chang, Shetou Township (TW); Yi-Shao Liu, Zhubei (TW); Chun-Ren Cheng, Hsinchu (TW); Chun-Wen Cheng, Zhubei (TW)

(73) Assignee: Taiwan Semiconductor Manufacturing Company, Ltd., Hsin-Chu (TW)

( * ) Notice: Subject to any disclaimer, the term of this patent is extended or adjusted under 35 U.S.C. 154(b) by 510 days.

This patent is subject to a terminal disclaimer.

(21) Appl. No.: 16/207,490

(22) Filed: Dec. 3, 2018

(65) Prior Publication Data

US 2019/0101531 A1 Apr. 4, 2019

Related U.S. Application Data

(60) Continuation of application No. 14/497,151, filed on Sep. 25, 2014, now Pat. No. 10,145,847, which is a
(Continued)

(51) Int. Cl.
*G01N 33/543* (2006.01)
*H01L 21/00* (2006.01)

(52) U.S. Cl.
CPC ....... *G01N 33/54386* (2013.01); *H01L 21/00* (2013.01); *H01L 2224/18* (2013.01)

(58) Field of Classification Search
None
See application file for complete search history.

(56) References Cited

U.S. PATENT DOCUMENTS

| 3,917,495 A | 11/1975 | Horn |
| 4,729,971 A | 3/1988 | Coleman |

(Continued)

FOREIGN PATENT DOCUMENTS

| DE | 69929042 T2 | 8/2006 |
| DE | 102007035633 A1 | 2/2009 |

(Continued)

*Primary Examiner* — Robert T. Crow
(74) *Attorney, Agent, or Firm* — Slater Matsil, LLP

(57) ABSTRACT

The present disclosure provides biochips and methods of fabricating biochips. The method includes combining three portions: a transparent substrate, a first substrate with microfluidic channels therein, and a second substrate. Through-holes for inlet and outlet are formed in the transparent substrate or the second substrate. Various non-organic landings with support medium for bio-materials to attach are formed on the first substrate and the second substrate before they are combined. In other embodiments, the microfluidic channel is formed of an adhesion layer between a transparent substrate and a second substrate with landings on the substrates.

20 Claims, 19 Drawing Sheets

Related U.S. Application Data division of application No. 13/801,182, filed on Mar. 13, 2013, now Pat. No. 8,846,416.

(56) References Cited

U.S. PATENT DOCUMENTS

| | | | |
|---|---|---|---|
| 6,036,872 | A | 3/2000 | Wood et al. |
| 6,271,102 | B1 | 8/2001 | Brouillette et al. |
| 6,426,183 | B1 | 7/2002 | Beattie |
| 6,635,226 | B1 | 10/2003 | Tso et al. |
| 7,972,875 | B2 | 7/2011 | Rogers et al. |
| 8,846,416 | B1 * | 9/2014 | Chu ................ H01L 21/00 438/1 |
| 10,145,847 | B2 * | 12/2018 | Chu ............. G01N 33/54386 |
| 2001/0023979 | A1 | 9/2001 | Brouillette et al. |
| 2004/0104454 | A1 | 6/2004 | Takaoka et al. |
| 2004/0258726 | A1 * | 12/2004 | Stupp ................ A61L 31/123 424/423 |
| 2006/0160249 | A1 | 7/2006 | Chou et al. |
| 2008/0219615 | A1 * | 9/2008 | Cunningham ........ B01L 3/5085 385/12 |
| 2009/0129986 | A1 * | 5/2009 | Wimberger-Friedl ................ B01L 3/502707 422/400 |
| 2011/0017593 | A1 | 1/2011 | Lee |
| 2011/0127681 | A1 | 6/2011 | Ni et al. |
| 2013/0061674 | A1 | 3/2013 | Reichenbach et al. |

FOREIGN PATENT DOCUMENTS

| | | |
|---|---|---|
| DE | 102007060632 A1 | 6/2009 |
| KR | 100785389 B1 | 12/2007 |
| KR | 100969671 B1 | 7/2010 |

\* cited by examiner

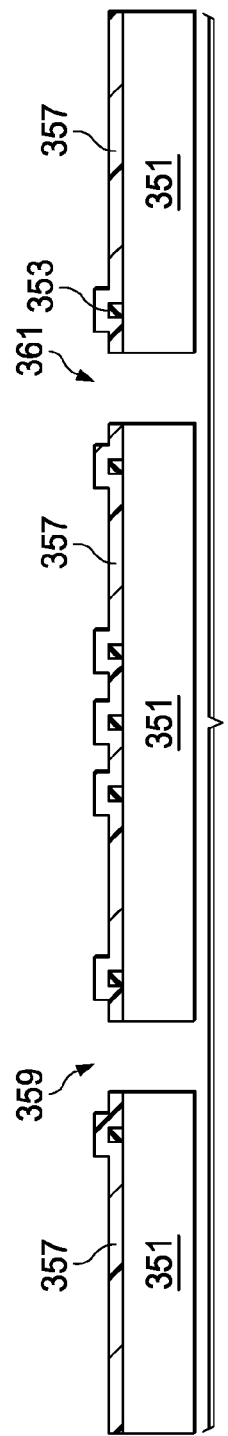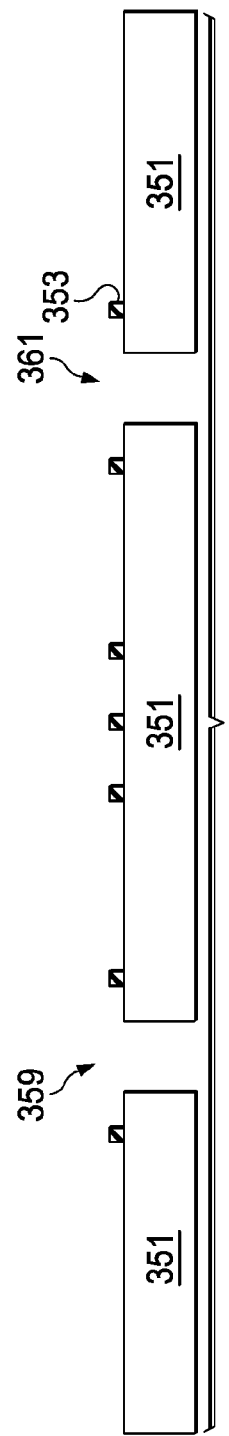

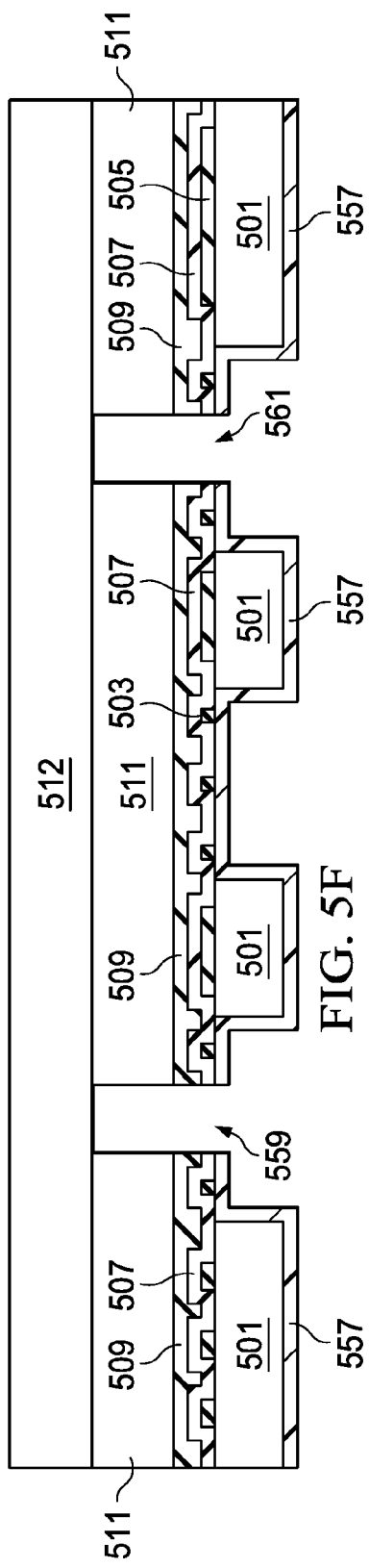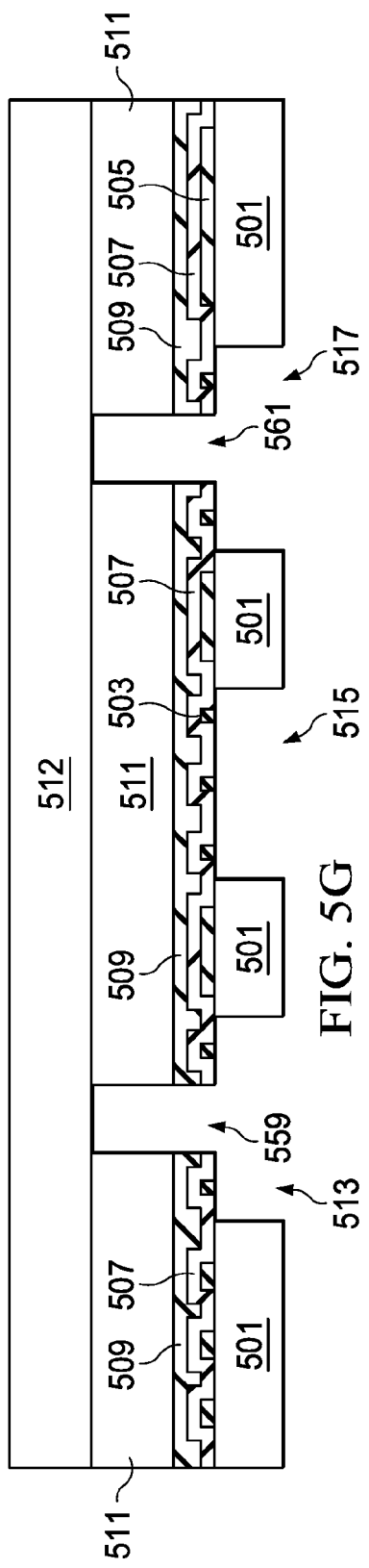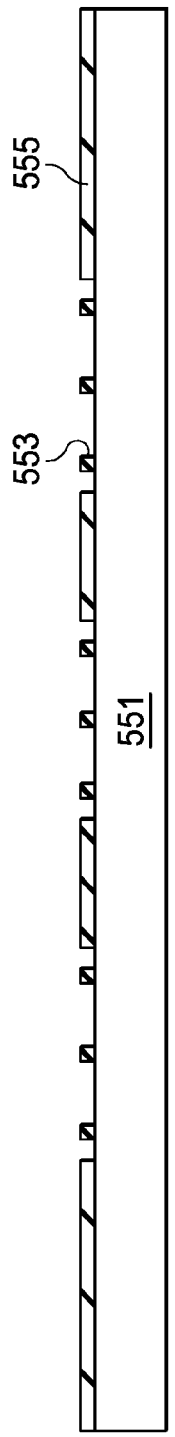

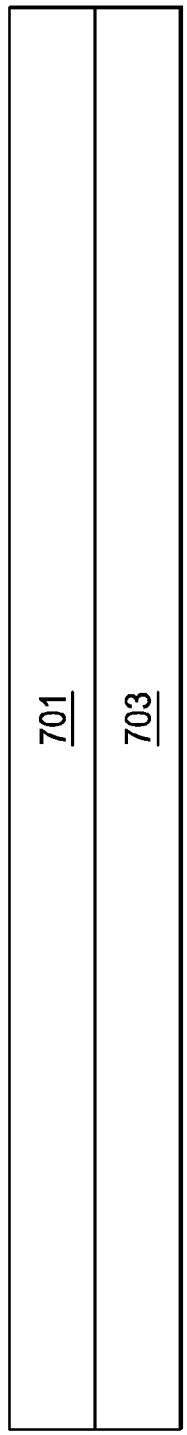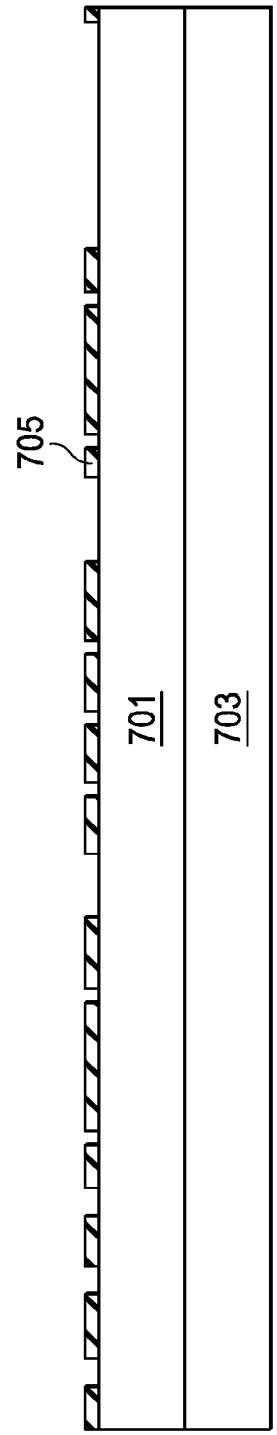

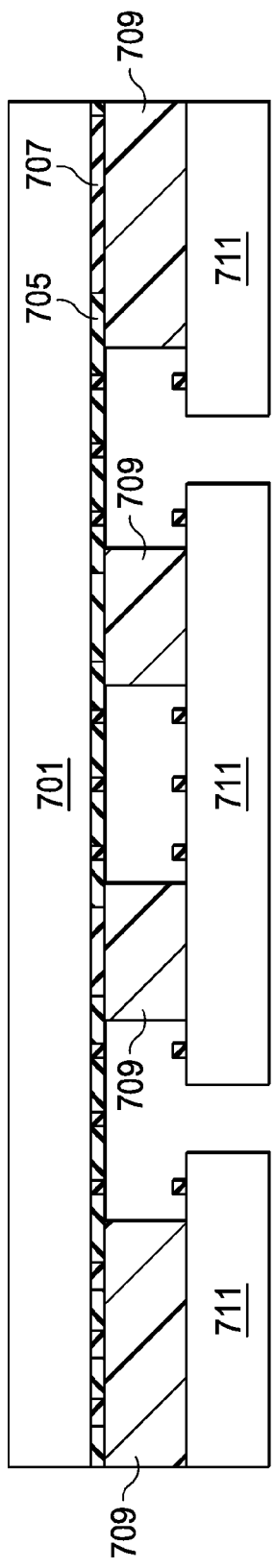
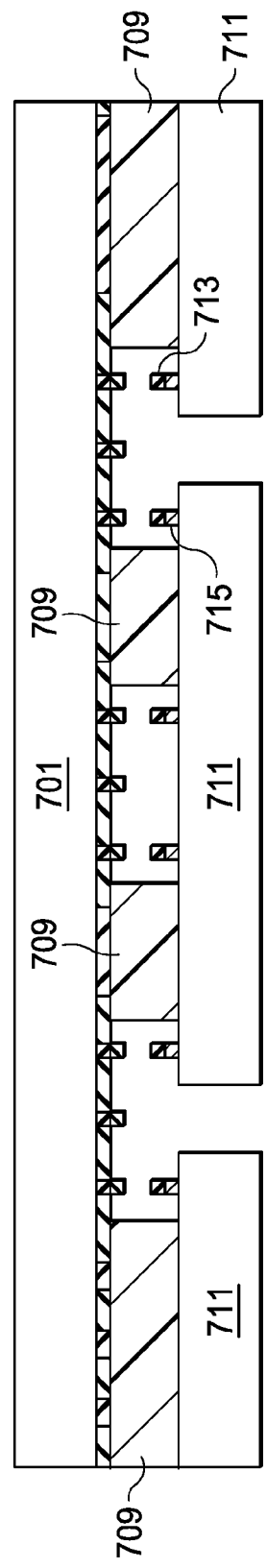
FIG. 7F
FIG. 7G

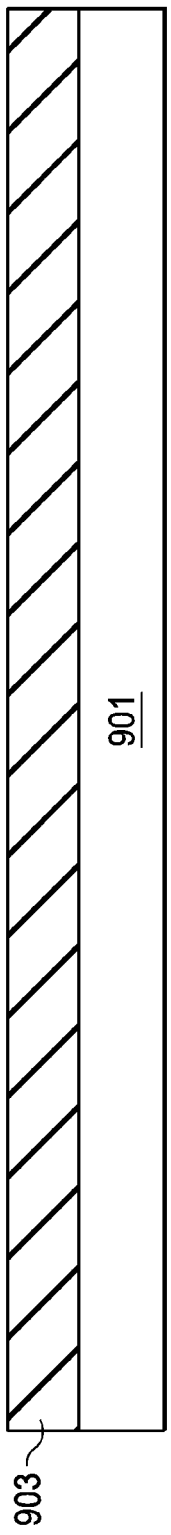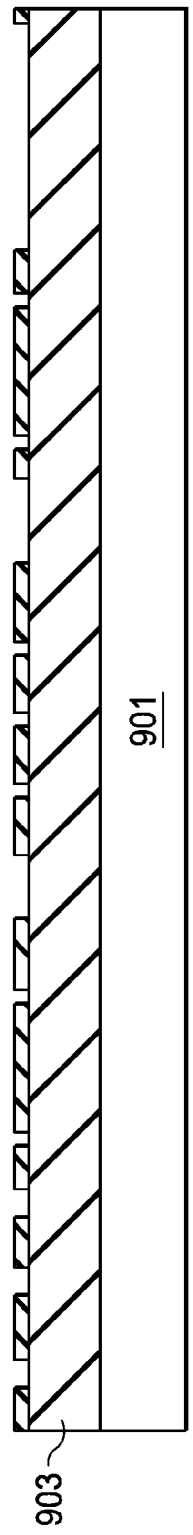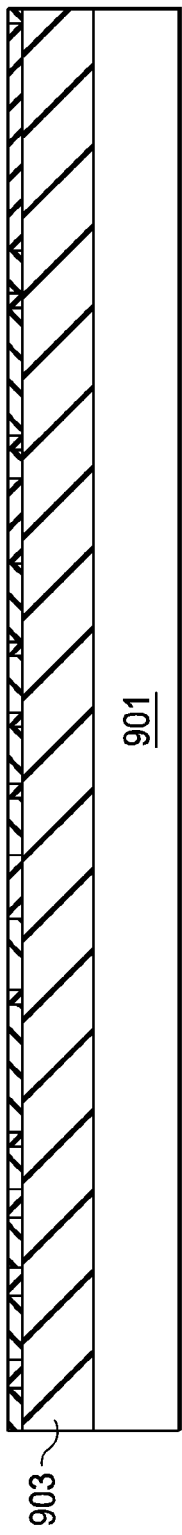

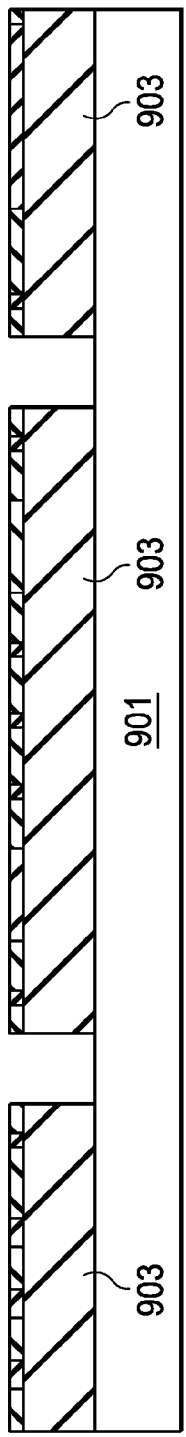
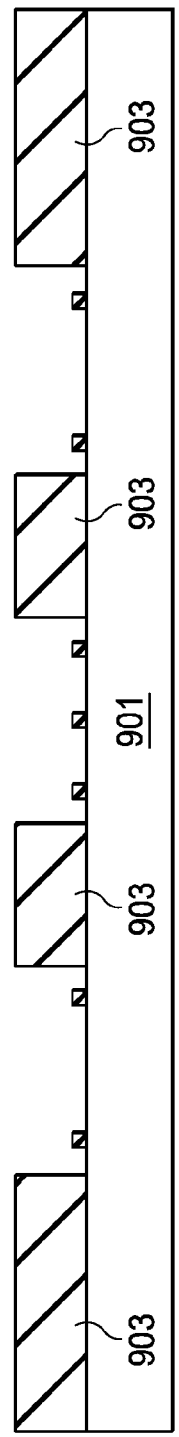

METHOD FOR FORMING BIOCHIPS AND BIOCHIPS WITH NON-ORGANIC LANDINGS FOR IMPROVED THERMAL BUDGET

PRIORITY

This application is a continuation of U.S. patent application Ser. No. 14/497,151, filed on Sep. 25, 2014, and entitled, "Method for Forming Biochips and Biochips With Non-Organic Landings for Improved Thermal Budget," which is a divisional of U.S. patent application Ser. No. 13/801,182, filed on Mar. 13, 2013, and entitled, "Method for Forming Biochips and Biochips With Non-Organic Landings for Improved Thermal Budget," now U.S. Pat. No. 8,846,416, issued Sep. 30, 2014, which applications are incorporated herein by reference.

FIELD

This disclosure relates to biosensors and methods for forming bio-chips. Particularly, this disclosure relates to bio-chips having biosensors and fluidic devices and methods for forming them.

BACKGROUND

Biosensors are devices for sensing and detecting biomolecules and operate on the basis of electronic, electrochemical, optical, and/or mechanical detection principles. Biosensors can sense charges, photons, and mechanical properties of bio-entities or biomolecules, or through molecular tags. The detection can be performed by detecting the bio-entities or biomolecules themselves, or through interaction and reaction between specified reactants and bio-entities/biomolecules. Such biosensors can be manufactured using semiconductor processes, and can be easily applied to integrated circuits (ICs) and microelectromechanical systems (MEMS).

Biochips are essentially miniaturized laboratories that can perform hundreds or thousands of simultaneous biochemical reactions, such as polymerase-chain reactions (PCR) including solid phase/bridge amplification. Biochips can detect particular biomolecules, measure their properties, process the signal, and may even analyze the data directly. Biochips enable researchers to quickly screen large numbers of biological analytes for a variety of purposes, from disease diagnosis to detection of bioterrorism agents. Advanced biochips use a number of biosensors along with fluidic channels to integrate reaction, sensing, and sample management. While biochips are advantageous in many respects, challenges in their fabrication and/or operation arise, for example, due to compatibility issues between the semiconductor fabrication processes, the biological applications, and restrictions and/or limits on the semiconductor fabrication processes.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

FIGS. 3A-3H are cross-sectional views of a biochip in accordance with various embodiments according to methods of FIG. 2 of the present disclosure.

FIGS. 5A-5L are cross-sectional views of a biochip in accordance with various embodiments according to methods of FIG. 4 of the present disclosure.

FIGS. 7A-7G are cross-sectional views of a biochip in accordance with various embodiments according to methods of FIGS. 6A and 6B of the present disclosure.

FIGS. 9A-9G are cross-sectional views of a biochip in accordance with various embodiments according to methods of FIG. 8 of the present disclosure.

DETAILED DESCRIPTION

Figure 1A:
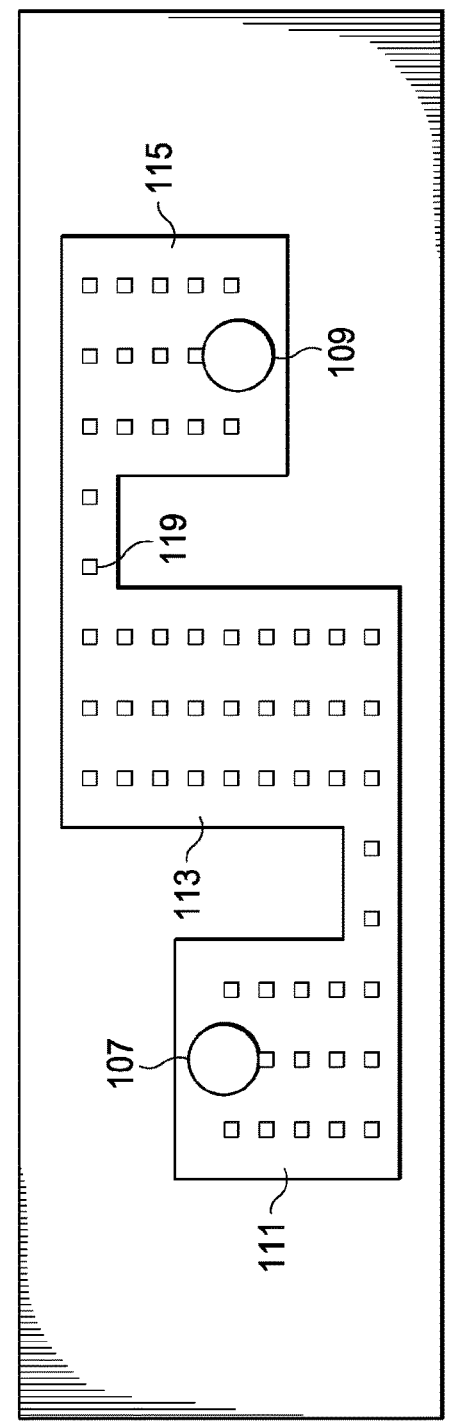
FIG. 1A is a top view of a biochip in accordance with various embodiments of the present disclosure.

It is to be understood that the following disclosure provides many different embodiments, or examples, for implementing different features of the invention. Specific examples of components and arrangements are described below to simplify the present disclosure. These are, of course, merely examples and are not intended to be limiting. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact. Further still, references to relative terms such as "top", "front", "bottom", and "back" are used to provide a relative relationship between elements and are not intended to imply any absolute direction. Various features may be arbitrarily drawn in different scales for simplicity and clarity.

A simple conventional biochip involves various bioreceptors which react with various biological material of interest in one or more patterned sites. One such reaction is the polymerase chain reaction (PCR) that can multiply by orders or magnitude the number of molecular strands at a site. Various approaches are used to differentiate among different reactants and reactions for detection. One common approach is to tag a reaction with a fluorescent or phosphorescent label that emits a detectible photon. A coordinated, or ordered array, approach would encode the sensor or bioreceptors to a location on the biochip, so that a positive reaction and photo-detection would be correlated to the location to determine the nature of the reaction, for example, identity of the biological material. In many cases, the location is externally observed by optical detection. In other cases, the location corresponds to embedded sensors that signal a measurement. The signal may be optical, magnetic, electrical, or a mass-sensitive measurement such as surface acoustic wave or microbalance weights. Another approach is the random approach that encodes the sensor with different fluorescence, phosphorescence, or otherwise detectible and differentiable tags. A positive detection would be correlated to the type of signal transduced to determine the nature of the detection. The signal transduced may be photons, for example, where a different wavelength of light is generated for different biological materials or reactions. In another example, surface plasmon resonance could be used to detect different biological materials without the use of fluorescent or phosphorescent tags or labels.

More advanced biochips involve not only biosensors, but also various fluidic channels to deliver biological material to the sensors. The fluidic channels may be a part of a microfluidic system that includes pumps, valves, and various measurement devices such as flow meters, pressure transducers, and temperature sensors. Combination of fluid processing and sensing is advantageously integrated within a semiconductor chip environment. A potential use of biochips is as a lab-on-a-chip—where medical professionals can use a small biochip to perform testing in the field, obtain results directly, and proceed with treatment or further analysis without retreating to a laboratory. Especially for medical professionals working in remote areas where sample preservation may be difficult, lab-on-a-chip devices can save lots of traveling and waiting. These lab-on-a-chip devices are often single-use, or disposable, devices. As such, the manufacturing costs have to be low to be economically viable.

Semiconductor processing often involves baking, curing, and exposing various surfaces to plasma energy and radiation energy. At high temperatures (i.e., above about 75 degrees Celsius, above 100 degrees Celsius, or over 150 degree Celsius) and/or high energies, these processes would damage or destroy organic bioreceptors and surface modification layers, which usually are delicate bio-molecules or very thin layers of surface chemistry. For example, the bioreceptors may be antibodies/antigens, enzymes, nucleic acids/DNA, cellular structures/cells, and biomimetic receptors. The surface modification chemistry may include layers of hexamethyldisilazane (HMDS), 3-aminopropyl triethoxysilane (APTES), agar, or hydrogel.

Thus, the bio-functionalization of surfaces on which bio-molecules are attached, are often performed after all the semiconductor processes are completed to avoid being exposed to the high temperature processes. In some designs, the fluidic channels are formed directly on the semiconductor substrate, usually silicon wafer and hereinafter referred to as the sensing wafer, along with bioreceptor sites, hereinafter referred to as landings. In other designs, the fluidic channels are formed on a fluidic substrate that is subsequently bonded to the sensing wafer having the landings. In some designs, the biosensors are embedded and integrated with the landings. In other designs, the biosensors are not intrinsically integrated with the landings. In such case, the fluidic channel has a transparent lid, which allows an external optical detection of biomolecules or reactions. In the case where the fluidic channel is on the sensing wafer, the fluidic channel formation, usually etching a trench or via into the substrate, can damage the biosensors, bioreceptors, or surface modification layer. To avoid this damage, when a high temperature bonding process is used, the bioreceptors are deposited on the interior walls of the fluidic channels after the bonding process and the fluidic channels are enclosed, usually by flowing through each biochip a high concentration of bioreceptors through the fluidic channel surfaces having some affinity for the bioreceptors. However, the density of bioreceptors that attach to the surfaces is hard to control, and the process is slow and wasteful of bioreceptors and reagents. In some cases, the bound-bioreceptor density varies throughout the biochip or a batch of biochips (not uniform) as the concentrations in the reagents change. The random, non-aligned locations and non-uniform concentrations complicate resolution of detectible activities at different sites using image processing algorithms. The locations may overlap each other and are hard to resolve. The randomness also makes difficult correlations between different biochips because each would have different bioreceptor mapping.

The various embodiments of the present disclosure contemplates a wafer-level process and a biochip that addresses many of these issues by providing non-organic landings that are resistant to high temperature processing as bioreceptors sites. The bioreceptors, for example, DNA primers, are attached to the landings after the biochip is fabricated. The site locations are patterned with an adhesive layer and a support medium to form the landings. The density issue as well as the random, non-aligned location issue are addressed by forcing the bioreceptors to attach only at the landing sites. The use of high-temperature resistance landings allow certain semiconductor processes to be used in fabricating the biochip that otherwise cannot be used. The various method embodiments of the present disclosure may be performed in a semiconductor fabrication facility and can be configured to be compatible with the complementary metal-oxide-semiconductor (CMOS) process. In more detail, the processing of materials on glass and etching of glass are often incompatible with some stages of the CMOS process because the glass processing can introduce particles that are considered contaminants for other CMOS processes. Some embodiments of the present disclosure involve no glass processing or minimal processing of glass when it is used as a transparent substrate. In some embodiments, the glass processing is performed separately from the other processes to avoid introduction of contaminants.

Figure 1B:
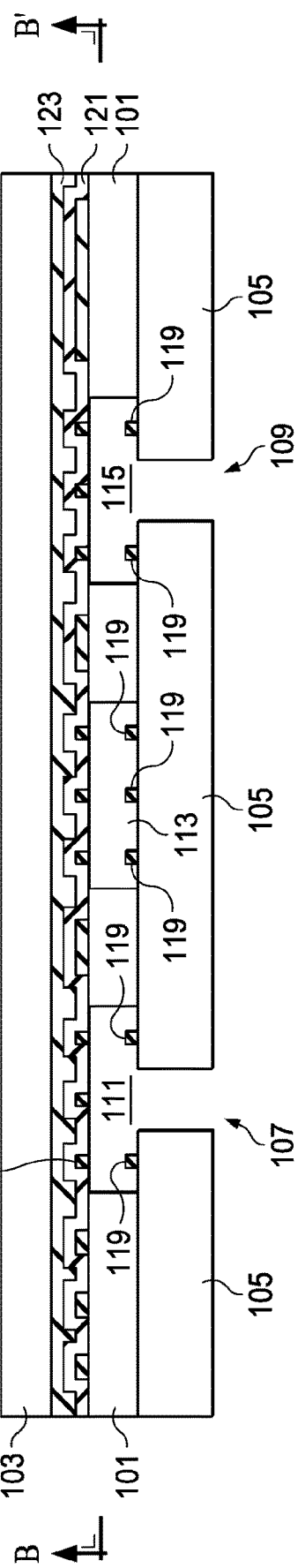
FIG. 1B is a cross section view of a biochip in accordance with various embodiments of the present disclosure.

In certain embodiments, the biochip of the present disclosure is formed by combining three substrates, at least one of which is transparent. FIG. 1A is a top view of a biochip 100 in accordance with some embodiments of the present disclosure. FIG. 1B is a cross-section of the biochip 100 from sectional line A-A' of FIG. 1A. The top view of FIG. 1A is cut from sectional line B-B' of FIG. 1B. Biochip 100 includes a first substrate 101 bonded to a transparent substrate 103 and a second substrate 105. The second substrate 105 has a fluidic inlet 107/109 and a fluidic outlet 109/107 through the second substrate 105. The first substrate 101 includes microfluidic channel patterns, shown as channels 111, 113, and 115. The various channels 111, 113, and 115 are connected to each other via various pathways and may be different sizes depending on the design of the biochip. The channels include various landings on top of the channels close to the transparent substrate 103 or bottom of the channels on the second substrate 105, or both. FIG. 1B shows the landings on both top and bottom of the channels. First landings 117 are formed on the first substrate 101 and surrounded by a passivating layer 121. Second landings 119 are formed on the second substrate 105. The first and second landings may have different densities in different channels. The landings have certain chemistries that allow some material to bind to it. In some cases, the landings may provide a hydrophilic, a hydrophobic, or another surface chemistry such as affinity for particular functional groups. According to various embodiments, a support medium on which various bio-materials can bind, including agar or polyethylene glycol (PEG) hydrogel, is disposed on the landings. The support medium is connected to the landing on the substrate through an adhesion layer, which may be 3-aminopropyl triethoxysilane (APTES), or hexamethyldisilazane (HMDS). The first landing 117 and second landings 119 on the substrate may be different materials to provide different chemistries. In some cases, the landings on the substrate are silicon oxide, certain metal oxides, or metal.

An oxide layer 123 covers the passivating layer 121 and is bonded to the transparent substrate 103. The first substrate 101 and the transparent substrate 103 are bound by an oxide-oxide binding process. The first substrate 101 and the second substrate 105 are bound by a silicon-silicon binding process. Very good adhesion is achieved without any chance of leakage for these bonds because no adhesive is used.

Figure 2:
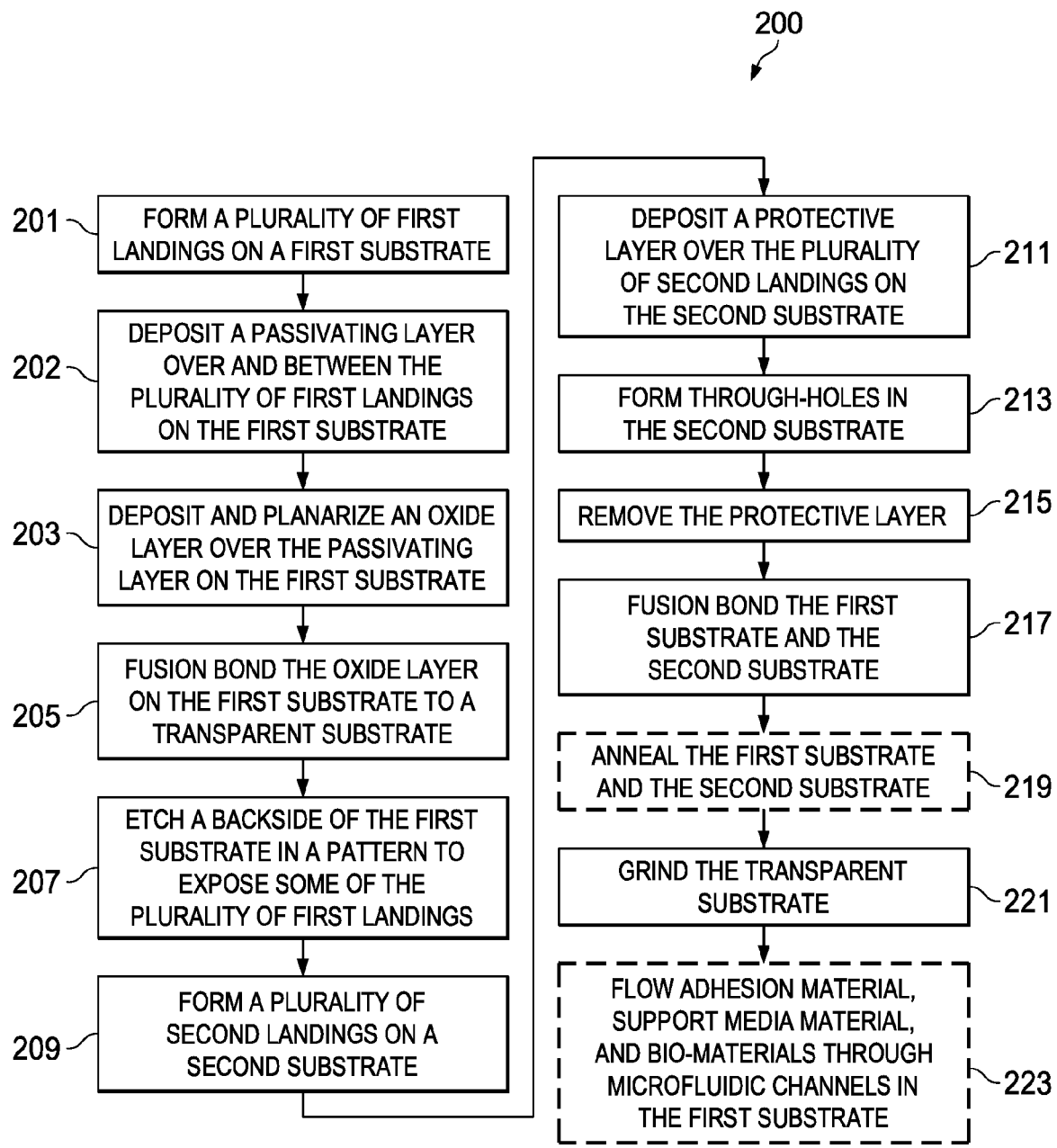
FIG. 2 is a flow chart of various embodiments of methods of fabricating a biochip device according to one or more aspects of the present disclosure.
Figure 3A:
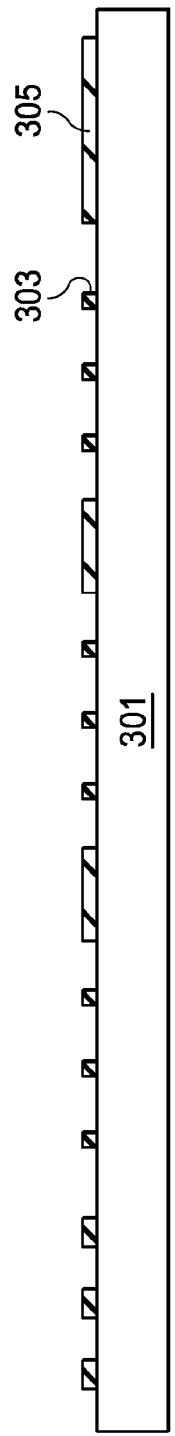

FIG. 2 is a flow chart of some embodiments of methods 200 of fabricating a biochip device according to one or more aspects of the present disclosure. FIGS. 3A to 3H are cross-sectional views of partially fabricated biochip devices constructed according to one or more steps of the method 200 of FIG. 2. In operation 201 of FIG. 2, a number of first landings is formed on a first substrate. FIG. 3A shows the first substrate 301. The first substrate 301 may be silicon, sapphire, silicon carbide, or other commonly used semiconductor substrates that does not react with the analyte or solution. In some embodiments, the first landings are formed by depositing an oxide layer and patterning the oxide layer. The oxide layer may be between about 100 nm and about 200 nm thick. The oxide layer may be doped or undoped silicon oxide or a metal oxide. The oxide layer pattern including first landings 303 and oxide blocks 305. The transparent substrate is subsequently attached to the first substrate through the oxide blocks 305.

In some embodiments, the first landings are not oxides. The first landings may be metal, for example gold or platinum that shows particular affinity for certain chemical groups or proteins. Metallic first landings are formed by depositing a layer of metal and patterning the metal layer by etching or depositing a patterned mask layer before depositing the metal layer, then removing the mask layer along with overlying metal in a lift-off operation.

Figure 3B:
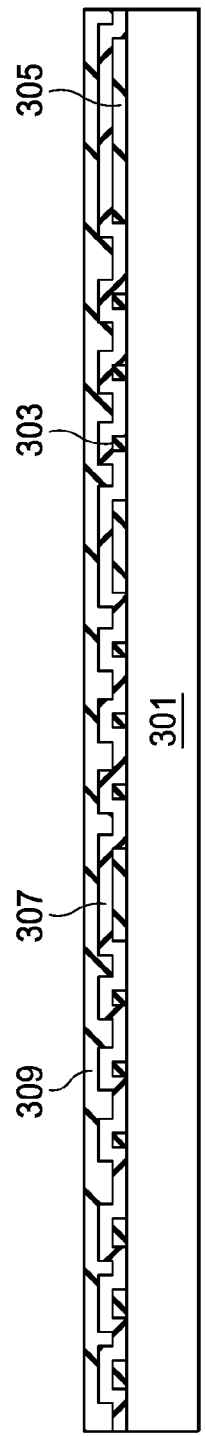

Referring back to FIG. 2, in operation 202, a passivating layer is deposited over and between the plurality of first landings on the first substrate. FIG. 3B shows a first substrate 301 with a passivating layer 307 over the first landings 303 and oxide blocks 305. The passivating layer 307 has a surface which does not attract or bind a biomaterial intended for a landing site. The passivating layer 307 may be silicon nitride at about 700 nm.

Figure 3C:
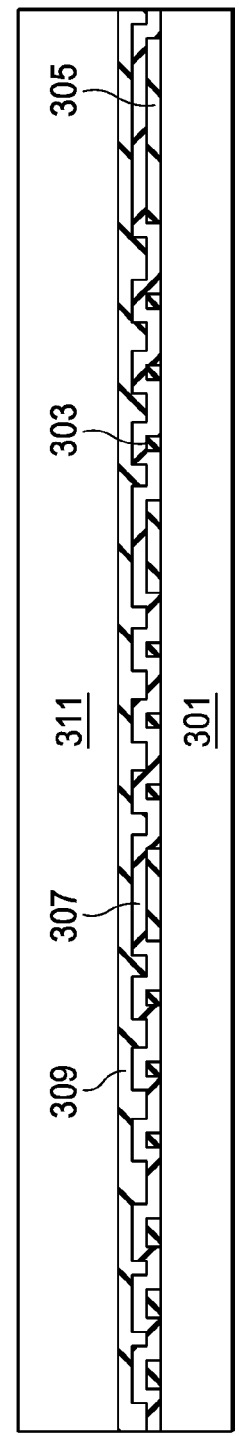

Referring back to FIG. 2, in operation 203 an oxide layer is deposited and planarized over the passivating layer on the first substrate. FIG. 3B shows the oxide layer 309 over the passivating layer 307. The oxide layer 309 may include the same material or different material from the first landing 303. After planarization, a thickness of at least one hundred nanometers (nm) remains. According to some embodiments, the oxide layer 309 is between about 300 and about 500 nm. The oxide layer 309 is planarized to ensure a smooth and flat surface for fusion bonding with a transparent substrate in operation 205 of FIG. 2. The transparent substrate may be glass, quartz, sapphire, or other transparent substrate. The oxide to glass bond may involve water between the oxide and glass and anneal at a temperature above 150 to 300 degrees Celsius. The glass substrate may be about 500 microns or thicker. FIG. 3C shows a transparent substrate 311 bonded to the oxide layer 309.

Figure 3D:
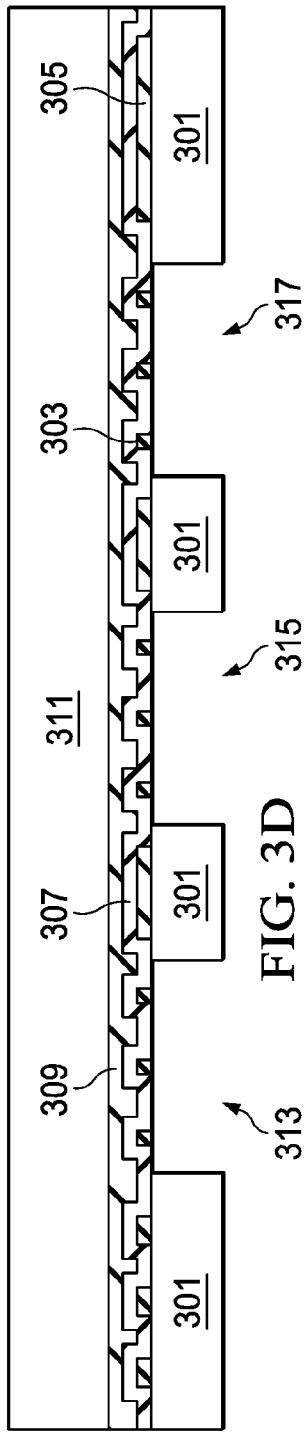

Referring back to FIG. 2, in operation 207 a backside of the first substrate is etched to expose at least some of the first landings. The openings are the microfluidic channels of the biochip. The first substrate may be thinned first by grinding to less than about 150 microns, or about 100 microns or less. A mask pattern is used to etch the first substrate from the backside and stop on the first landing and passivating layers. In some embodiments, a wet etch involves potassium hydroxide (KOH), tetramethylammonium hydroxide (TMAH), or ethylene diamine and pyrocatechol (EDP). The selection of different etchant involves the type amount of silicon to be etched, as the etch rates differ, and the thickness of first landing and passivating layers. A thick first landing, for example, about 200 nm or greater, allows some over etching to occur without risk to removing the first landing altogether. The silicon plane to be etched affects the etch selectivity among different etchants. One skilled in the art would choose the wet etch process appropriate for the situation. In other embodiments, a dry etch involving fluorine or chlorine-containing plasma is used through a mask pattern. The dry etch results in less undercutting of the silicon under the etch mask. However, a small amount of over etching of the first landing and passivating layers is expected. FIG. 3D is the cross section of a partially fabricated biochip with microfluidic channels 313, 315, and 317 formed by etching into first substrate 301. The first landings 303 and portions of the passivating layer 307 are exposed in the bottom of the microfluidic channels 313, 315, and 317.

Figure 3E:
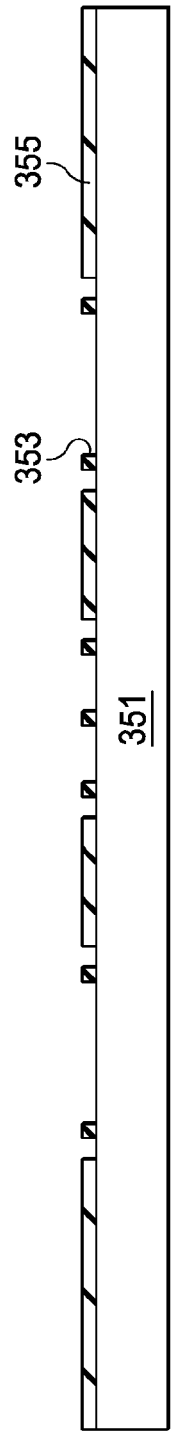

Referring back to FIG. 2, in operation 209 a plurality of second landings are formed on a second substrate. The second substrate may be silicon, sapphire, silicon carbide, or other commonly used semiconductor substrates that does not react with the analyte or solution. The different ways to form the second landings are the same as the ways described to form the first landings in association with operation 201. In short, a layer is either patterned by etching or deposited into a pattern and lifted-off. The second landings may be of a same material as the first landing or different material and the formation process may be same or different. FIG. 3E shows the second substrate 351 having second landings 353 and blocks 355 thereon.

The second substrate may be a sensing wafer containing sensing and microfluidic machines for fluid processing. Sensors such as temperature sensor, pressure transducer, and flow meter may be fabricated first on the sensing wafer along with microfluidic machines such as pumps and valves. In some embodiments, the sensing wafer includes electrodes and magnets for directing fluid flow and for separating certain components of the analyte. The sensing wafer may also include localized heaters at each landing or for a group of landings. Separate controls for the localized heaters allow different amplification of bio-materials for testing. The heater may be embedded in the substrate under the landing or disposed on the substrate surface close to the landing.

Figure 3F:
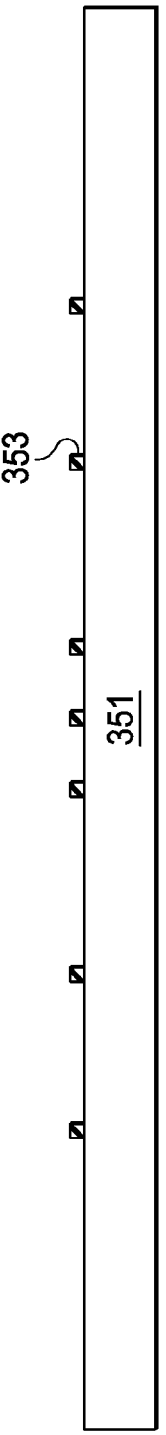

The blocks 355 may be removed by wet etching in a separate, optional operation to expose a fusion bonding area under the blocks. If performed, a separate etch mask is used to perform the wet etching. This operation may be performed if the blocks on the second substrate surface after patterning in operation 209 cannot be used directly for fusion bonding. As understood, fusion bonding can have defects and create voids between the substrates bonded if the substrate surface is not flat and particle-free. The blocks on the second substrate may contain etch residues not favorable for fusion bonding. Wet etching can completely remove the block 355 to form a second substrate surface suitable for fusion bonding. FIG. 3F shows the second substrate 351 with only the second landings 353 thereon after the blocks 355 have been removed.

Referring to FIG. 2, in operation 211 a protective layer is deposited over the plurality of second landings on the second substrate. The protective layer is material layer that separates any laser drilling byproduct from the substrate and the landings. The protective layer is easily removed from the substrate. According to various embodiments, the protective layer is Skycoat or Nanoshelter, both available from Nikka Seiko Co., Ltd of Tokyo, Japan. In other examples, the protective layer is silicon nitride or water-soluble wax. The protective layer is generally deposited in a fluid phase, either liquid or vapor, onto the second substrate surface. In some embodiments, the protective layer is water soluble and is cleaned away along with any deposits thereon easily. In other embodiments, the protective layer reacts with another chemical to form a gas and any deposits thereon can be vacuumed away. A silicon nitride protective layer is removed using a hot phosphoric acid bath.

Referring to FIG. 2, in operation 213, through-holes are formed in the second substrate. In some embodiments, the through-holes are formed by laser drilling, microblasting, or ultrasonic drilling. Other techniques of forming through-holes include various etching techniques and waterjet drilling. Laser drilling of cylindrical holes generally occurs through melting and vaporization (also referred to as "ablation") of the substrate material through absorption of energy from a focused laser beam. Depending on the direction of the laser energy, the laser drilled through-holes can have the inverse trapezoidal shape in a cross section. Microblasting removes material by driving a high velocity fluid stream of air or inert gases of fine abrasive particles, usually about 0.001 in (0.025 mm) in diameter. Ultrasonic drilling involves using high frequency vibrations to hammer a bit through materials. At least two through-holes are formed for every biochip—an inlet and an outlet. More than two through-holes may be used for different inlet fluids or if the biochip performs separation of the analyte and more than one outlet is used. Depending on the process used for forming the through-holes, by products of the drilling may be attached to the protective layer. FIG. 3G is a cross sectional diagram of the second substrate 351 having a protective layer 357 over the second landings 353 and two through-holes 359 and 361.

Referring to FIG. 2, in operation 215, the protective layer is removed. As discussed in association with operation 211, the protective layer removal depends on the type of protective layer used. The protective layer may be removed by rinsing, steam cleaning, wet etching, and exposing the substrate to particular chemical vapors, heat, or radiation. Any deposits on the protective layer from the drilling operation are removed along with the protective layer. FIG. 3H is a cross sectional diagram of the second substrate 351 having second landings 353 and two through-holes 359 and 361.

Referring to FIG. 2, in operation 217, the first substrate and the second substrate are fusion bonded. The fusion bonding attaches the first substrate of FIG. 3D to second substrate of FIG. 3H to form the workpiece of FIG. 1B. According to various embodiments, the first substrate is silicon and the second substrate is also silicon. A silicon-to-silicon fusion bond involves bonding two silicon surfaces based on intermolecular interactions including van der Waals forces, hydrogen bonds, and strong covalent bonds. The two substrates are aligned and moved close together. If the surfaces are sufficiently smooth, the substrates start to bond as soon as they get in atomic contact. If the surface is activated by plasma to form silanol groups, at room temperature a significant fraction of Si—OH (silanol) groups start to form Si—O—Si and water. The formed water molecules will migrate or diffuse along the interface during a subsequent annealing process. In some circumstances, the substrates may be covered with water molecules so the bonding happens between chemisorbed water molecules on the opposing substrates surfaces. According to various embodiments, methods to enhance fusion bonding include plasma, ultra high vacuum, and chemical-mechanical polishing (CMP).

In optional operation 219, the first substrate and the second substrate are annealed. The anneal may be optional depending on the surface treatment and type of silicon surface bonded. A post-bond anneal is above 300 degree Celsius and may be over 700 degree Celsius. At over 300 degrees Celsius, covalent Si—Si bonds start to establish between the two substrate surfaces. At 700 degrees Celsius, newly established Si—Si bonds can reach cohesive strengths of bulk silicon. The annealing temperature depends on desirable bond strength and different pretreatments. In one example, one or more substrate is exposed to a plasma, fusion bonded, and then annealed at about 500 to about 800 degrees Celsius.

Referring to FIG. 2, in operation 221 the transparent substrate is grinded. In one-example, the transparent substrate is grounded to about 300 microns. The transparent substrate may be glass. The grinding process stresses the oxide-oxide bond between the transparent substrate and the first substrate and the silicon-silicon bond between the first substrate and the second substrate and may separate these substrates if defects and voids reduce the bonding strength.

In optional operation 223, adhesion, support medium, and bio-materials are flowed separately through the microfluidic channels in the first substrate. The adhesion, support medium, and bio-materials enter the microfluidic channels through one of the through-holes through the second substrate and exit the microfluidic channels through the other through-holes in the second substrate. Referring to FIG. 1A, in some embodiments, the adhesion, support medium, and bio-materials enter the biochip at through-hole 107 and flows through channels 111, 113, and 115 before exiting the biochip at through-hole 109. The various landings 117 and 119 are exposed to the adhesion, support medium, and bio-materials. The flow may be in vapor or liquid phase. As the adhesion, support medium, and bio-material flows through the channels, the materials sequentially adhere to the landing sites, which may be the first landings or the second landings, and avoid other regions, for example, the protective layer 121 and inner surface of the first substrate 101 and second substrate 105.

The adhesion material may be 3-aminopropyl triethoxysilane (APTES) or hexamethyldisilazane (HMDS). For example, APTES selectively adheres only to the first and second landing features that are hydrophilic to form an adhesion layer. In a second flow, a support media material is flowed through the channels and adheres to the adhesion layer to form the support medium. The support media material may be agar or hydrogel, for example, polyethylene glycol (PEG) hydrogel. In a third flow, short pieces of single stranded DNA known as primers are flowed through and attached to the support medium. In a subsequent flow, longer single stranded DNA are flowed through to hybridize with the primers. According to some embodiments, these longer strands can be amplified in population using various PCR techniques at the landing to form clusters. Some of the strands may have fluorescent tags that become activated by the reaction. When exposed to light, the fluorescent tags produce a light response that can be detected through the transparent substrate. An optical detection mechanism can detect the wavelength and intensity of light to determine the extent of reaction and population of the DNA strands.

After populating the landings with selected bio-materials, the biochip is used in the field or laboratory. In one example, the biochip is used to test for the presence of certain DNA strands. While FIG. 1A shows a simple flow path for the bio-material, the present disclosure also envisions much more complicated flow paths where some bio-material may be lysed, separated, dyed, and then tested or analyzed using chemical, electrical, or optical means. For example, a drop of blood may be inserted in an inlet and initially separated by plasma and cell type. Certain cells in the blood drop may be lysed. Some macromolecules in the lysate may be further broken down for analysis by downstream in the flow path. When more than one inlet and outlet through-holes are used, different bio-materials having different chemistries may attach to specific or corresponding landing sites.

Figure 4:
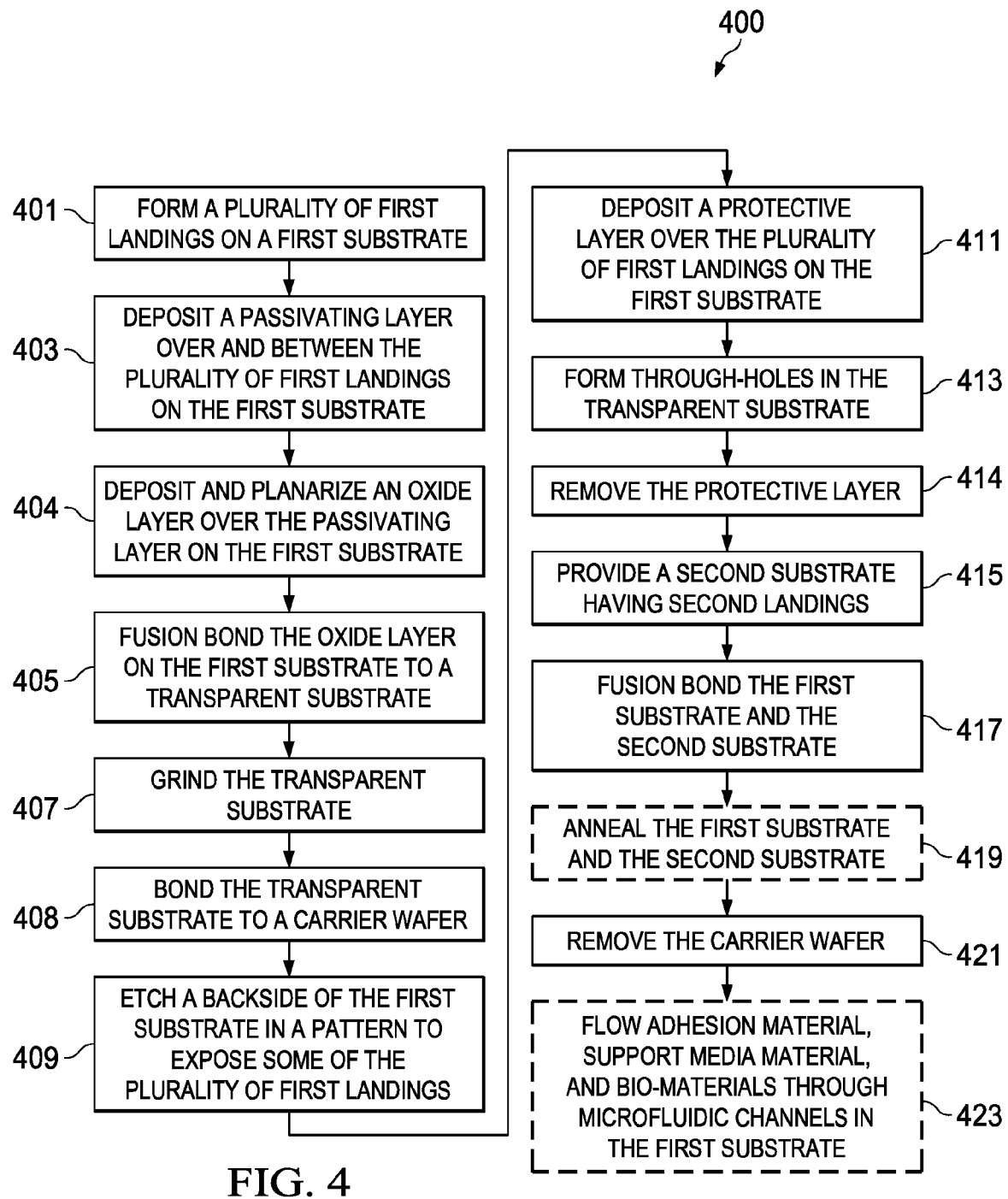
FIG. 4 is a flow chart of various embodiments of methods of fabricating a biochip device according to one or more aspects of the present disclosure.
Figure 5A:
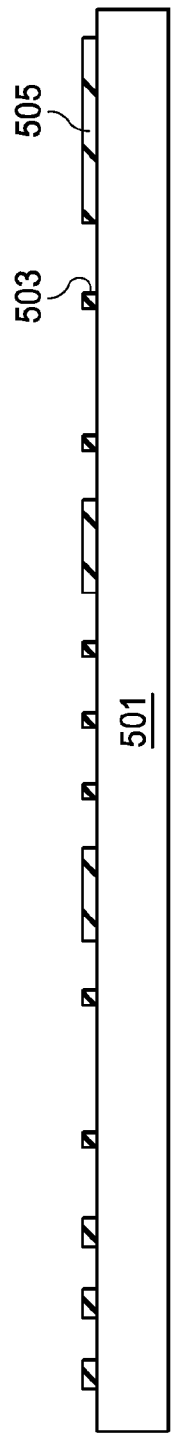

FIGS. 1A-1B, 2, 3A-3H, and associated text pertains to embodiments where the biochip inlet and outlet through-holes are located in the second substrate, which is on the opposite of the transparent substrate. In certain embodiments, the biochip inlet and outlet through-holes are located in the transparent substrate instead of the second substrate. The orientation of the optical detection determines the side of the transparent substrate to allow external observation of internal reactions. FIGS. 4 and 5A-5L show the embodiments where the through-holes are in the transparent substrate. In still other embodiments, the one of the through-holes, for example, the inlet, is on top, and the other through-hole, for example, the outlet, is on the bottom. The transparent substrate may be on either side. FIG. 4 shows a method 400 for forming a biochip in accordance with various embodiments of the present disclosure. FIGS. 5A to 5L are cross sectional diagrams of partially fabricated biochips after various operations of method 400. Because some of the operations of method 400 are very similar or the same as the operations of method 200, the similarities are merely referenced and not discussed in detail and differences are emphasized. In operation 401 of method 400 in FIG. 4, a number of first landings are formed on a first substrate. Operation 401 is the same as operation 201 of FIG. 2. FIG. 5A shows the first substrate 501 having first landings 503 and oxide blocks 505.

Figure 5B:
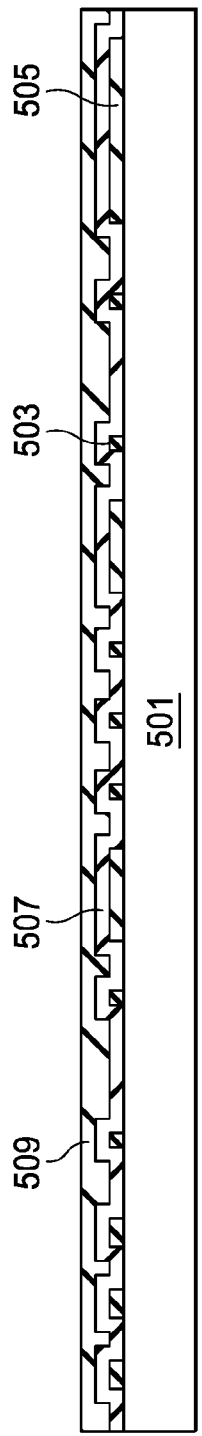

In operation 403, a passivating layer is deposited over and between the first landings on the first substrate. Operation 403 is the same as operation 202 of FIG. 2. FIG. 5B shows the first substrate 501 having first landings 503, oxide blocks 505, and a passivating layer 507 deposited over and between the first landings. Next, in operation 404, an oxide layer is deposited and planarized over the passivating layer on the first substrate. Operation 404 is the same as operation 203 of FIG. 2. FIG. 5B shows the oxide layer 509 over the passivating layer 507.

Figure 5C:
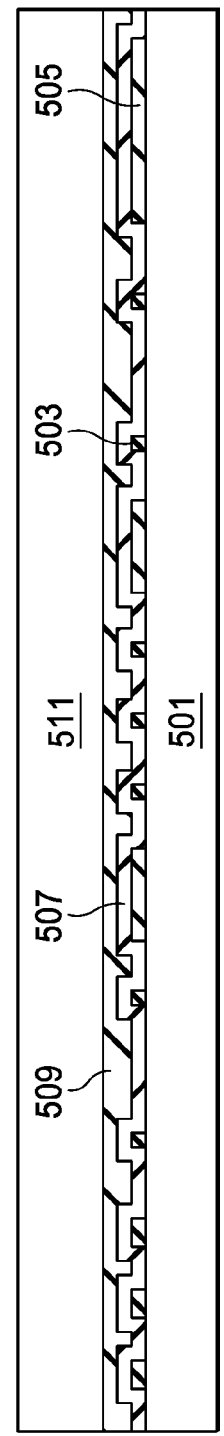

Referring back to FIG. 4, in operation 405 the oxide layer on the first substrate is fusion bonded to a transparent substrate. Operation 405 is the same as operation 205 of FIG. 2. After the fusion bonding, the transparent substrate is grinded in operation 407. The grinding operation 407 is similar to operation 221 of FIG. 2; however, the grinding operation 407 is performed before the second substrate is attached. A transparent substrate may be about 500 microns or thicker and is grinded to less than about 200 microns, or about 175 microns. FIG. 5C shows a first substrate 501 fusion bonded to a thinned transparent substrate 511.

Figure 5D:
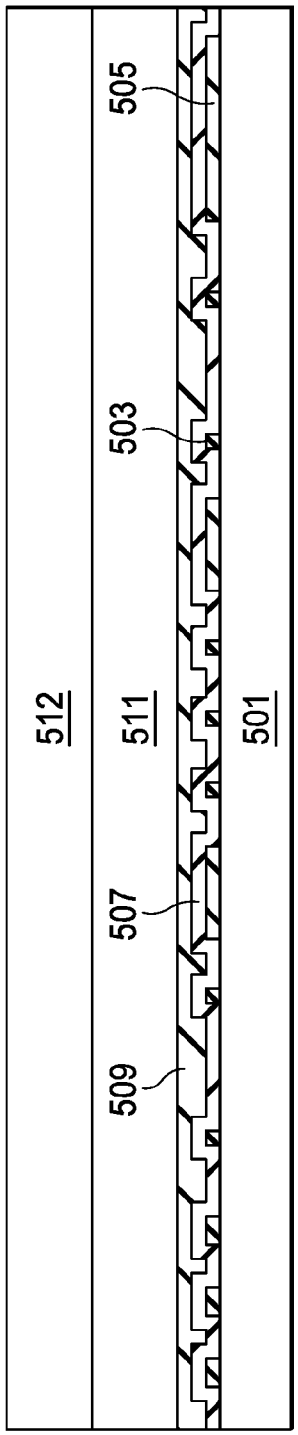

In operation 408 of FIG. 4, the transparent substrate is bonded to a carrier wafer. The carrier wafer allows further processing on the backside of the first substrate. The carrier wafer may be glass, a recycled silicon wafer, or another commonly used and recyclable carrier wafer. The bonding between the transparent substrate and carrier wafer is a temporary bond. The temporary bond is strong enough to withstand grinding of the first substrate and can be removed relatively easily. In some embodiments, an ultraviolet (UV) sensitive adhesive is used between the carrier wafer and the transparent substrate. The adhesive breaks down upon UV exposure. In other embodiments, the adhesion readily dissolves upon exposure to certain chemicals, while the certain chemicals do not affect other portions of the biochip. FIG. 5D shows the carrier wafer 512 attached to the transparent substrate 511, which is attached to the first substrate 501.

Figure 5E:
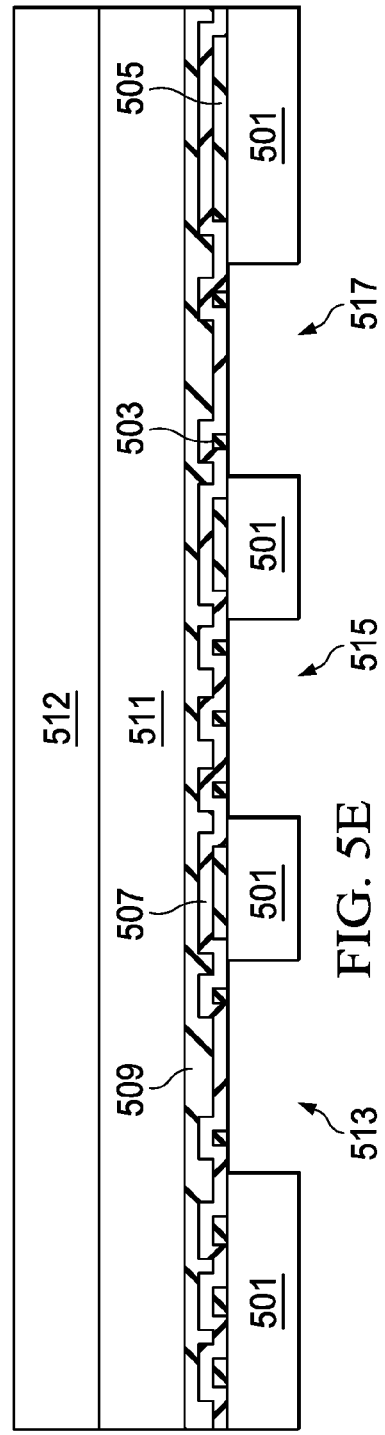

Referring back to FIG. 4, in operation 409 a backside of the first substrate is etched to expose at least some of the first landings. Operation 409 is the same as operation 207 of FIG. 2. The first substrate may be thinned first by grinding to less than about 150 microns, or about 100 microns or less. FIG. 5E is the cross section of a partially fabricated biochip with microfluidic channels 513, 515, and 517 formed by etching into first substrate 501. The first landings 503 and portions of the passivating layer 507 are exposed in the bottom of the microfluidic channels 513, 515, and 517.

Referring back to FIG. 4, in operation 411 a protective layer is deposited over the first landings on the first substrate. The operation 411 is similar to operation 211 of FIG. 2, but the protective layer is applied to a different substrate. In operation 411, the protective layer is applied to a backside of the first substrate having microfluidic channels that exposes the first landings. The protective layer ensures that by products from a drilling process would not affect the first substrate surface quality.

In operation 413, through-holes are formed in the transparent substrate through the protective layer, passivating layer, and the oxide layer. While through-holes are also formed in operation 213, the substrates are different and different process parameters apply. In operation 413, the through-hole is formed by laser drilling or ultrasonic drilling. A laser can focus its beam at a specific depth and do not puncture through the carrier wafer. On the other hand, other drilling methods, such as microblasting, may damage the carrier wafer and render it unrecyclable. In some embodiments, ultrasonic drilling is used. If the adhesive between the carrier wafer and the first substrate can sufficiently dampen the ultrasound such that the carrier wafer is not damaged, then ultrasonic drilling may be used. In other embodiments, the carrier wafer is not recycled and may be used to absorb any excess energy from the drilling operation. One skilled in the art would adjust the process to form the through-holes in cross section diagram of FIG. 5F showing the first substrate 501 having a protective layer 557 over the first landings 503 and two through-holes 559 and 561.

Referring back to FIG. 4, in operation 414 the protective layer is removed. Operation 414 is the same as operation 215 of FIG. 2. FIG. 5G is a cross section of the partially fabricated biochip without the protective layer. The partially fabricated biochip includes the first substrate 501, having microfluidic channels 513, 515, and 517 and through-holes 559 and 561 in the transparent substrate 511 but not through the carrier wafer 512.

Figure 5I:
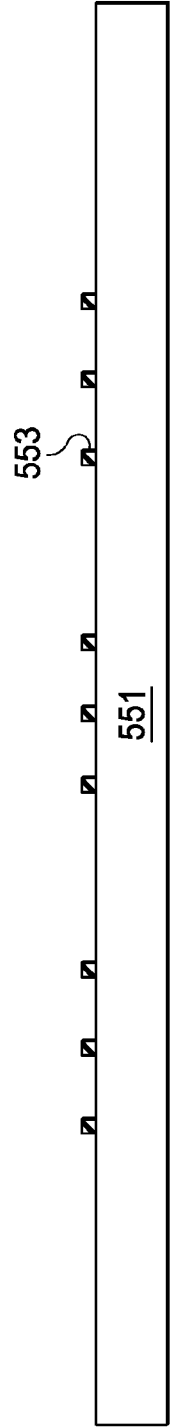

Referring back to FIG. 4, in operation 415 a second substrate having second landings is provided. If the second landings are formed by the same entity that formed the first landings, then operation 415 is the same as operation 209 of FIG. 2. FIG. 5H shows the second substrate 551 having second landings 553 and blocks 555 thereon. In other embodiments, second substrates are provided by a different entity that forms the second landings. The second landings may or may not be the same material as the first landings. Just as with method 200, the blocks 555 may not be formed or is removed by wet etching to expose a fusion bonding area under the blocks 555. The removal operation is the same as that described in association with operation 209 of FIG. 2. FIG. 5I shows the second substrate 551 with only the second landings 553 thereon after the blocks 555 have been removed.

Figure 5J:
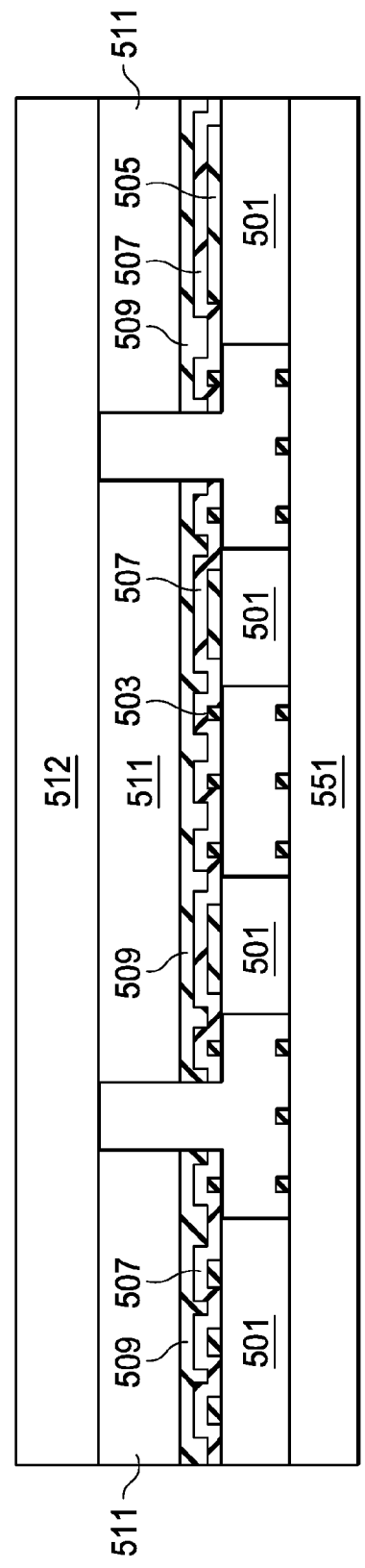

Referring back to FIG. 4, in operation 417, the first substrate and the second substrate are fusion bonded. This fusion bonding operation 417 is similar to operation 217 of FIG. 2. The location of through-holes and the presence of carrier wafer may change the fusion bonding process. Operation 417 is preferably completed in a vacuum environment. When the first substrate and the second substrate come into contact, the microfluidic channels are sealed within the biochip because the through-holes are covered by the carrier wafer. When the fusion bonding is completed at ambient pressure, air may be trapped under pressure and can cause the substrates to separate if heated. FIG. 5J shows the bonded substrates (workpiece), with second substrate 551 at one side, first substrate 501 adjoining the second substrate 551, transparent substrate 511 next to the first substrate 501, and carrier wafer 512 on the opposite side from the second substrate 551.

Referring back to FIG. 4, in operation 419, the first substrate, second substrate, transparent substrate, and carrier wafer are annealed. The anneal operation 419 is the same as operation 219 of FIG. 2, with the addition of carrier wafer in the anneal. As long as the various substrates have similar coefficients of thermal expansion (CTEs), the addition of carrier wafer does not affect the anneal process.

In operation 421, the carrier wafer is removed. The carrier wafer may be removed by reacting the adhesive chemically or optically, or by decomposing the interface layer. In some embodiments, the workpiece is exposed to a vapor or liquid that reacts or dissolves the adhesive. In other embodiments, the adhesive is exposed to a radiation that breaks it down chemically, for example, an UV light. In still other embodiments, a short burst of laser focused at the interface between the carrier wafer and the transparent substrate can be used to de-bond the two. Regardless of method, care must be taken to not damage the transparent substrate surface. While the transparent substrate surface can be polished if damaged, the through-hole openings on the transparent substrate would have to be plugged to avoid damage inside the microfluidic channels.

Figure 5K:
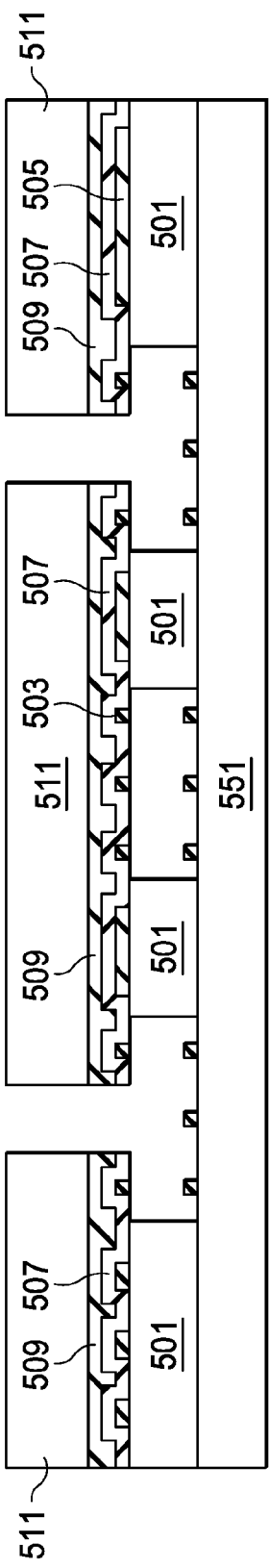

In some embodiments, operations 419 and 421 may be switched. If the fusion bonding without anneal has a high enough bond strength to withstand the carrier wafer de-bonding, then the carrier wafer may be removed first. Switching the order of operations 419 and 421 may be performed especially when the adhesive between the carrier wafer and the transparent substrate would harden during the anneal. FIG. 5K shows the partially fabricated biochip after the carrier wafer has been removed.

Figure 5L:
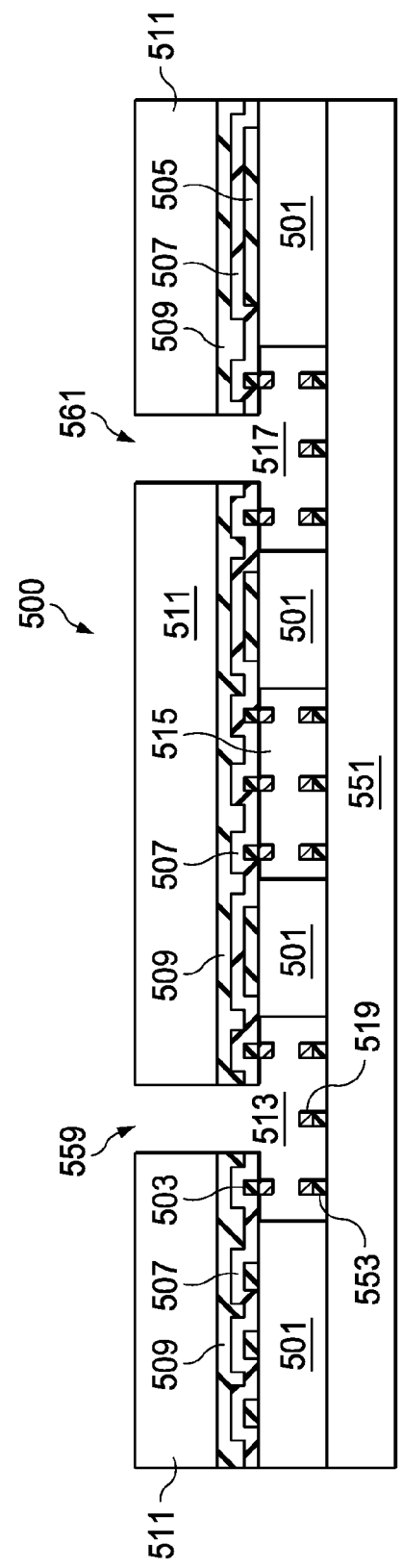

Referring back to FIG. 4 in operation 423, bio-materials may be flown through the microfluidic channels in the first substrate. Operation 423 is the same as operation 223 of FIG. 2. FIG. 5L shows the biochip 500 having a second substrate 551, a first substrate 501 bonded to the second substrate 551, and a transparent substrate 511 bonded to the first substrate 501. Microfluidic channels 513, 515, and 517 are formed through the first substrate 501, which is the sidewalls. Through-holes 559 and 561 connect to the microfluidic channels through the transparent substrate 511 and portions of an oxide layer 509 and a passivating layer 507 on the first substrate 501. In a top view, the microfluidic channels 513, 515, and 517 connect to each other. The microfluidic channels include first landings 503 and second landings 553 on opposite sides. The first landings 503 are on the side of transparent substrate 511 and exposed by etching away the first substrate under the first landings 503. The passivating layer 507 surrounds the first landings. An oxide layer 509 bonds the transparent substrate 511 to the first substrate 501. The bio-materials 519 adhere to the first and second landings 503/553 and can be used to bio-functionalize the biochip.

Figures 6A, 6B:
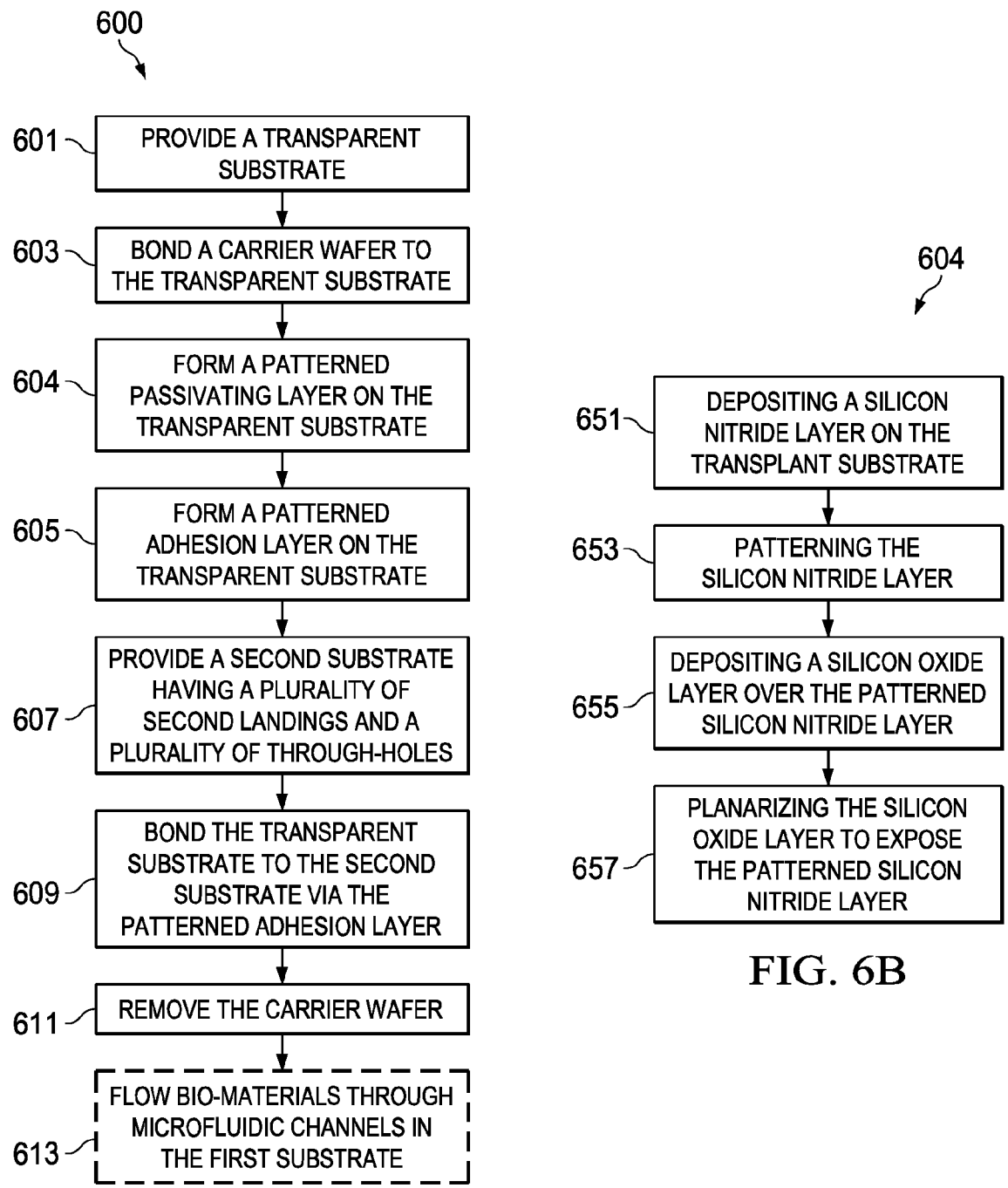
FIGS. 6A and 6B are flow charts of various embodiments of methods of fabricating a biochip device according to one or more aspects of the present disclosure.

The following embodiments are processes of forming biochips and biochips that do not include a first substrate as the microfluidic channel structure. Instead, the sidewalls of the microfluidic channel structure are formed by depositing and patterning another material. FIGS. 6A/6B and 7A to 7G show embodiments where the through-holes are in the second substrate. FIGS. 8 and 9A to 9G show embodiments where the through-holes are in the transparent substrate. Because some of the operations of these embodiments are very similar or the same as the operations of embodiments employing a first substrate, the similarities are merely referenced and not discussed in detail and differences are emphasized.

In operation 601 of method 600 in FIG. 6A, a transparent substrate is provided. The transparent substrate may be glass, quartz, sapphire, or other transparent substrate. In operation 603 a carrier wafer is bonded to the transparent substrate. The bonding operation 603 is the same as operation 408 of FIG. 4, except that the transparent substrate here is a blank substrate with no patterned structures thereon. FIG. 7A shows the transparent substrate 701 bonded to a carrier wafer 703.

In operation 604, a patterned passivating layer is formed on the transparent substrate. The first passivating layer may be a silicon nitride pattern formed by depositing a layer of silicon nitride and patterning the silicon nitride. The patterning including depositing a photoresist, exposing a light pattern on the photoresist, developing the photoresist, using the remaining photoresist to etch the silicon nitride, and removing the remaining photoresist. The exposed transparent substrate between the silicon nitride patterns is the landing for bio-materials. FIG. 7B shows a transparent substrate 701 with a patterned passivating layer 705 thereon.

Figure 7C:
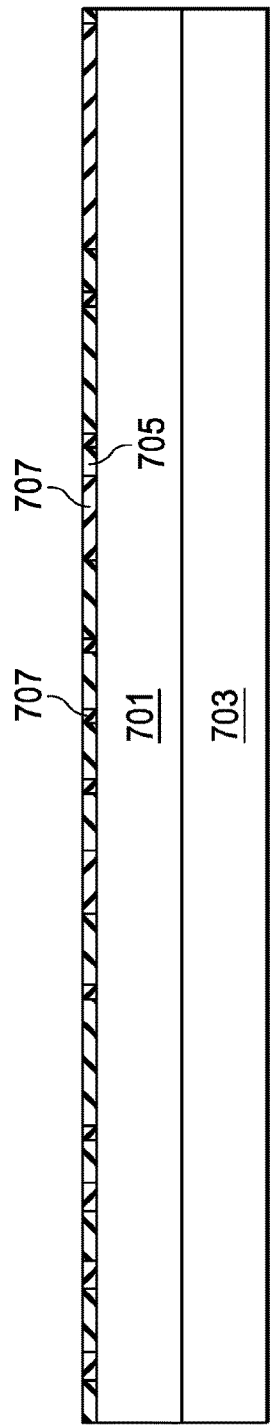

FIG. 6B is a process flow diagram of operation 604 in some embodiments. In operation 651, a silicon nitride layer is deposited on the transparent substrate. The silicon nitride may be deposited using one of chemical vapor deposition (CVD) techniques. In operation 653, the silicon nitride layer is patterned. The patterning may be performed using lithographic techniques. In operation 655 a silicon oxide layer is deposited over the patterned silicon nitride layer. The silicon oxide fills the area between the silicon nitride patterns as well as over the silicon nitride pattern. In operation 657, the silicon oxide layer is planarized to expose the patterned silicon nitride layer. In other words, the silicon oxide layer deposited over the patterned silicon nitride is removed. The patterned silicon nitride is the passivating layer. The silicon oxide is the landing sites. FIG. 7C shows a transparent substrate 701 having a patterned silicon nitride 705 and silicon oxide landing 707. The patterned silicon nitride 705 and the silicon oxide landing 707 have a planar top surface.

Figure 7D:
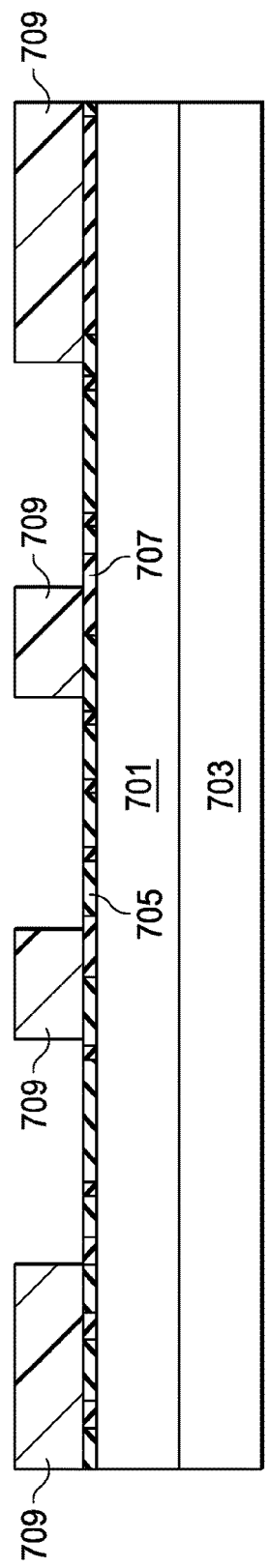

Referring back to FIG. 6A, in operation 605 a patterned adhesion layer is formed on the transparent substrate. The patterned adhesion layer may be any bio-compatible adhesive, glue, polymer, epoxy, bonder, or solder that can provide a hermetic seal to form channels and wells. The material may be a photoresist, a silicone, a thermoplastic, or various insulators with added adhesion material. The adhesion layer, after patterning, is the sidewalls of the microfluidic channels. According to some embodiments, the depth or height of the sidewalls may be as much as 100 microns or greater. The adhesion layer is compatible with CMOS processes and may be easily patterned. Photoresist material can be designed to have different surface viscosities and use different deposition process parameters to form a relatively uniform film over the substrate and can be a suitable adhesion layer. One such example is SU-8. Another example is poly(phenylmethyl)silsesquioxane (PSQ). Silicone material may be molded and shaped to various shapes and sizes. Once hardened, silicone material can provide a hydrophobic or hydrophilic surface as fluid channels. In some embodiments, a silicone material polydimethylsiloxane (PDMS) is patterned by a soft lithography process. The PDMS is poured over a wafer having desired sidewall shapes etched into it and hardened. The PDMS is then removed and sealed to a glass substrate by activating the PDMS surface using RF plasma. In other embodiments, the PDMS is molded using compression molding or injection molding directly on the first substrate. Thermoplastic materials can also be patterned using soft lithography or molding processes. Suitable thermoplastic material includes poly(methyl methacrylate) (PMMA), polycarbonate (PC), and polyimide (PI). Various insulators may be deposited and patterned using semiconductor processes. For example, silicon oxide, silicon nitride, or various commonly used insulators in semiconductor processing may be used. The sidewall structure material may have more than one layers. In some embodiments, the first layer adds thickness while the second or subsequent layers add adhesion properties and/or surface chemistry. FIG. 7D is a cross section diagram including a patterned adhesion layer 709 over the patterned silicon nitride 705 and the silicon oxide landing 707.

Figure 7E:
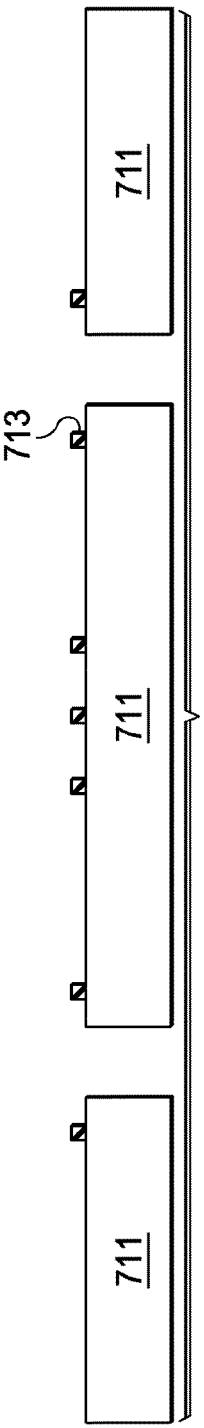
Figure 8:
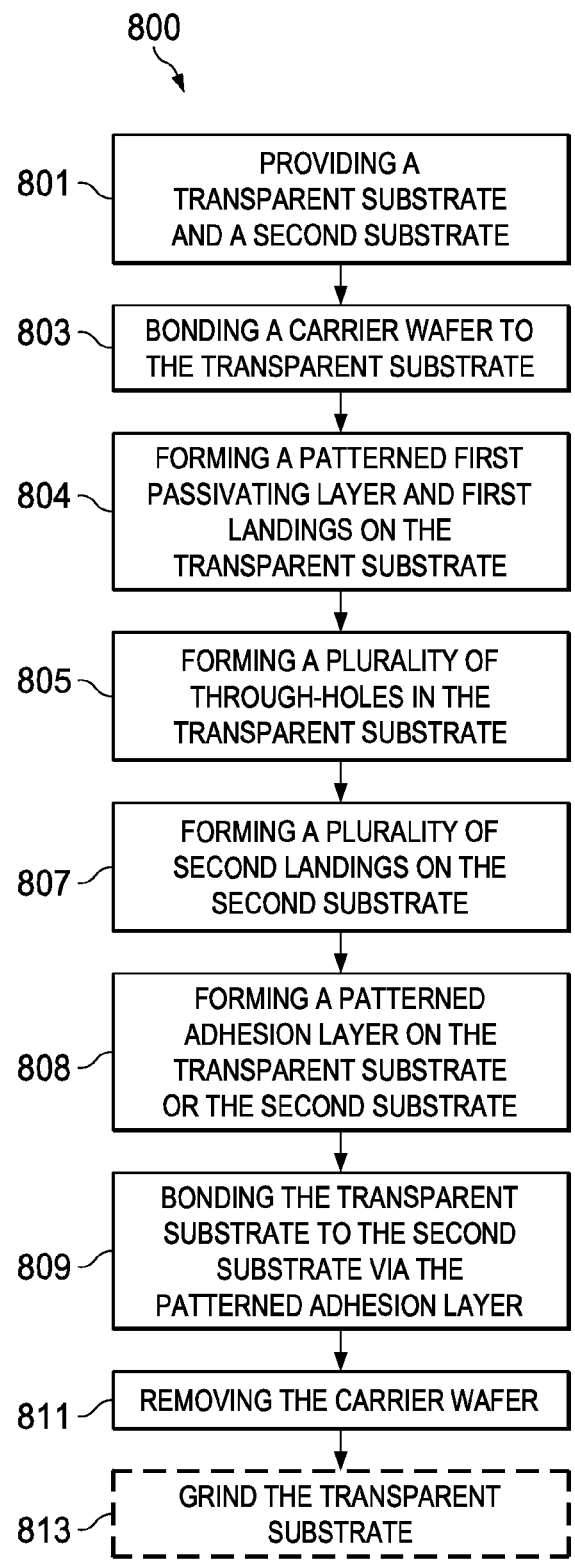
FIG. 8 is a flow chart of various embodiments of methods of fabricating a biochip device according to one or more aspects of the present disclosure.

Referring back to FIG. 6A, in operation 607 a second substrate having second landings and a plurality of through-holes is provided. Such second substrate and formation has been described with respect to the method embodiments of FIG. 2 and FIG. 4. For example, the operations 209, 211, 213, and 215 of method 200 results in a second substrate having second landings and a plurality of through-holes, as shown in FIG. 3H. In other embodiments, the second substrate is formed by a different entity and the second substrate is provided. FIG. 7E shows the second substrate 711 with second landings 713 thereon.

Referring back to FIG. 6A, in operation 609 the transparent substrate is bonded to the second substrate via the patterned adhesion layer. Depending on the type of adhesion layer, it may be activated first before bonding. Activation may include exposure to plasma, gas/vapors, fluid, heat, or radiation. Because the energy-sensitive bio-material has not been introduced, the patterned adhesion layer activation is not limited to low energy methods. In the example of PSQ, an oxygen plasma breaks bonds on the PSQ surface and creates dangling bonds which readily adhere to a silicon oxide, a thin layer of which is always present on a silicon wafer exposed to ambient conditions. In the example of APTES, water catalyzes covalent bonds between APTES and a silicon-containing substrate at room temperature. The second substrate and the transparent substrate are aligned and brought into proximity of each other during the bonding process. Mechanical pressure may be applied to one or more of the substrates to ensure good contact. The bonding process may involve specific vacuum and temperature parameters. After the initial bonding, additional steps may be taken to strengthen the bond such as curing under high temperature and exposure to certain radiation.

The carrier wafer is removed in operation 611 of FIG. 6A. The carrier wafer is removed by the process described in association with operation 421 of method 400 in FIG. 4. FIG. 7F shows the second substrate 711 bonded to the transparent substrate 701 via the patterned adhesion layer 709. The carrier wafer is removed.

Referring back to FIG. 6A, in operation 613, support media material and bio-materials may be flown through the microfluidic channels in the first substrate. Operation 613 is the same as operation 223 of FIG. 2. FIG. 7G shows bio-material 715 attached to the first landings 707 and second landings 713.

Figure 9F:
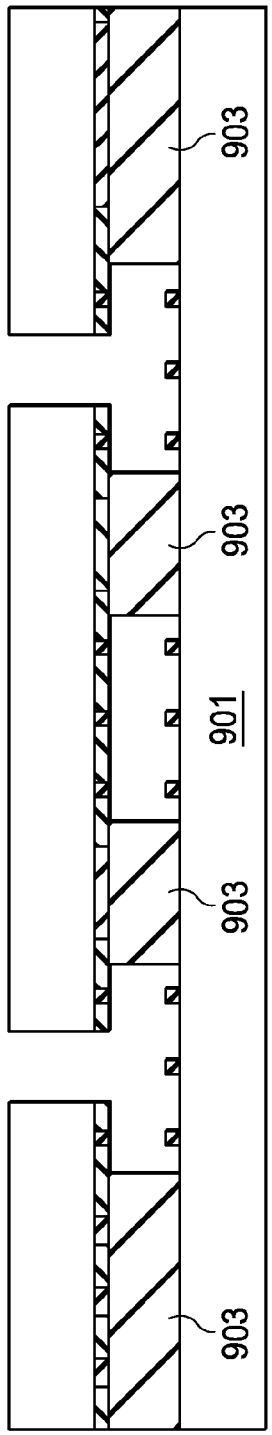
Figure 9G:
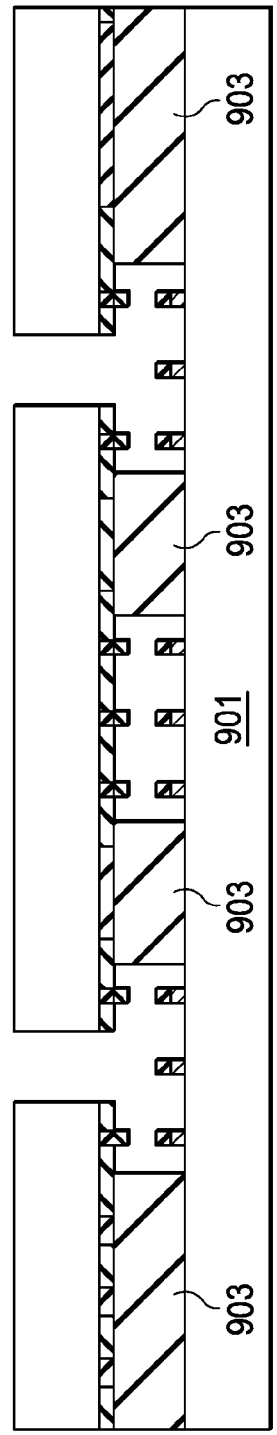

In other embodiments, FIGS. 8 and 9A to 9G show methods and structure where the through-holes are in the transparent substrate instead of the second substrate. These embodiments involve various process operations that are already discussed in relation to different embodiments. Operations 801 and 803 are the same as operations 601 and 603 of FIG. 6A. In operation 804, a patterned first passivating layer and first landings are formed on the transparent substrate. Operation 804 is similar to operations 651 to 657 as discussed in association with FIG. 6B. FIGS. 9A, 9B, and 9C are the same as FIGS. 7A, 7B, and 7C. In operation 805, through-holes are formed in the transparent substrate. Operation 805 is similar to operation 413 and associated FIG. 9D is similar to FIG. 5F that is associated with operation 413. The transparent substrate of operation 413 has a patterned passivating layer and first landings and is bonded to a first substrate.

Referring back to FIG. 8, in operation 807, second landings are formed on the second substrate. Operation 807 is the same as operation 209 of FIG. 2. In operation 808, patterned adhesion layers are formed on the transparent substrate or the second substrate. Operation 808 is the same as operation 605 of FIG. 6, with an additional choice of substrate. In some embodiments, the patterned adhesion layer is formed on both substrates. In FIG. 9E, the patterned adhesion layer 903 is formed on the second substrate 901.

Referring back to FIG. 8, in operation 809 the transparent substrate is bonded to the second substrate via the patterned adhesion layer, as shown in FIG. 9F. While the patterned adhesion layer may be on the transparent substrate or the second substrate, this operation is the same as operation 609. In operation 811, the carrier wafer is removed. Operation 811 is the same as operation 611 of FIG. 6A. Optionally in operation 813, the transparent substrate is grinded as in operations 221 and 407. Finally, bio-material may be flowed in the biochip and attached as in FIG. 9G.

One aspect of the present disclosure pertains to a method of manufacturing a biochip that includes forming first landings on a first substrate, depositing a passivating layer over and between the first landings on the first substrate, depositing and planarizing an oxide layer over the passivating layer on the first substrate, fusion bonding the oxide layer on the first substrate to a transparent substrate, etching a backside of the first substrate in a pattern to expose some of the first landings, forming second landings on a second substrate, depositing a protective layer over the second landings on the second substrate, forming through-holes in the second substrate, removing the protective layer, and fusion bonding the first substrate and the second substrate. The method may also include flowing adhesion layer material, support media material, and bio-material sequentially through the through-holes and fluidic channels to attach them to the first and second landings.

Another aspect of the present disclosure pertains to a method of manufacturing a biochip. The method includes forming first landings on a first substrate, depositing a passivating layer over and between the plurality of first landings on the first substrate, depositing and planarizing an oxide layer over the passivating layer on the first substrate, fusion bonding the oxide layer on the first substrate to a transparent substrate, grinding the transparent substrate, bonding the transparent substrate to a carrier wafer, etching a backside of the first substrate in a pattern to expose some of the plurality of first landings, depositing a protective layer over the exposed plurality of first landings and the first substrate, forming through-holes in the transparent substrate, removing the protective layer, fusion bonding the first substrate and a second substrate having a plurality of second landings thereon, and removing the carrier wafer. The method may also include flowing adhesion layer material, support media material, and bio-material sequentially through the through-holes and fluidic channels to attach them to the first and second landings.

In yet another aspect, the present disclosure pertains to a method of making a biochip. The method includes providing a transparent substrate, bonding a carrier wafer to the transparent substrate, forming a patterned passivating layer and first landings on the transparent substrate, forming a patterned adhesion layer on the transparent substrate, providing a second substrate having second landings and through-holes, bonding the transparent substrate to the second substrate via the patterned adhesion layer, and removing the carrier wafer. The method may also include flowing adhesion layer material, support media material, and bio-material sequentially through the through-holes and fluidic channels to attach them to the first and second landings. The bio-materials adhere to the first and second landings.

In some aspects, the present disclosure pertains to a method of making a biochip. The method includes providing a transparent substrate and a second substrate, bonding a carrier wafer to the transparent substrate, forming a patterned passivating layer and first landings on the transparent substrate, forming second landings on the second substrate, forming a patterned adhesion layer on the transparent substrate or the second substrate, forming through-holes in the transparent substrate, bonding the transparent substrate to the second substrate via the patterned adhesion layer, and removing the carrier wafer. The method may also include flowing adhesion layer material, support media material, and bio-material sequentially through the through-holes and fluidic channels to attach them to the first and second landings.

The present disclosure also pertains to a biochip having a transparent substrate and a bottom substrate, which may or may not be transparent. Microfluidic channels are disposed between the transparent substrate and the bottom substrate. The sidewalls of the microfluidic channels may be formed of a first substrate different from the bottom substrate or formed of a patterned adhesion layer. The top, bottom, or both top and bottom of the microfluidic channels include first landings and second landings configured to bond to bio-materials which attach to the landings after the biochip is formed.

In describing one or more of these embodiments, the present disclosure may offer several advantages over prior art devices. In the discussion of the advantages or benefits that follows it should be noted that these benefits and/or results may be present is some embodiments, but are not required in every embodiment. Further, it is understood that different embodiments disclosed herein offer different features and advantages, and that various changes, substitutions and alterations may be made without departing from the spirit and scope of the present disclosure.

What is claimed is:

1. A biochip comprising:
   a transparent substrate;
   a patterned passivating layer on the transparent substrate;
   a patterned adhesion layer on the transparent substrate;
   a second substrate bonded to the transparent substrate, the second substrate having a plurality of first landings, wherein the biochip comprises a microfluidic channel having the patterned adhesion layer as a sidewall, wherein the microfluidic channel comprises:
      a first opening extending fully through the second substrate, the first opening being surrounded by a material of the second substrate;
      a second opening extending fully through the second substrate, the second opening being different from the first opening and being surrounded by the material of the second substrate; and
      a connecting portion connecting the first opening and the second opening, wherein each opening into the connecting portion is surrounded by the material of the second substrate in a top down view, wherein the first landings overlie an exposed portion of the transparent substrate.

2. The biochip of claim 1, further comprising second landings embedded within the patterned passivating layer.

3. The biochip of claim 2, wherein the first landings have a first density and the second landings have a second density different from the first density.

4. The biochip of claim 2, wherein the first landings comprise a first material and the second landings comprise a second material different from the first material.

5. The biochip of claim 1, wherein the second substrate has a thickness of between about 100 nm and about 200 nm.

6. The biochip of claim 1, wherein the first landings are non-organic.

7. The biochip of claim 6, wherein the first landings comprise a metal.

8. A biochip comprising:
   a transparent substrate;
   a patterned passivating layer on the transparent substrate;
   a patterned adhesion layer to the transparent substrate;
   a second substrate bonded to the transparent substrate, the second substrate having a plurality of first landings, wherein the biochip comprises a microfluidic channel having the patterned adhesion layer as a sidewall, wherein the second substrate is a sensing wafer, wherein the microfluidic channel comprises:
      a first opening extending fully through the second substrate, the first opening being surrounded by a material of the second substrate;
      a second opening extending fully through the second substrate, the second opening being different from the first opening and being surrounded by the material of the second substrate; and
      a connecting portion connecting the first opening and the second opening, wherein each opening into the connecting portion is surrounded by the material of the second substrate in a top down view, wherein the first landings overlie an exposed portion of the transparent substrate.

9. The biochip of claim 8, wherein the sensing wafer further comprises a temperature sensor.

10. The biochip of claim 9, wherein the sensing wafer further comprises a heater.

11. The biochip of claim 10, further comprising a pump.

12. The biochip of claim 11, further comprising an embedded sensor.

13. The biochip of claim 12, wherein the embedded sensor is an optical sensor.

14. A biochip comprising:
a transparent substrate;
a patterned passivating layer on the transparent substrate;
a patterned adhesion layer on the transparent substrate;
a second substrate bonded to the transparent substrate, the second substrate having a plurality of first landings, wherein the biochip comprises a microfluidic channel having the patterned adhesion layer as a sidewall, wherein the microfluidic channel comprises:
a first opening extending fully through the second substrate, the first opening being surrounded by a material of the second substrate;
a second opening extending fully through the second substrate, the second opening being different from the first opening and being surrounded by the material of the second substrate;
a connecting portion connecting the first opening and the second opening, wherein each opening into the connecting portion is surrounded by the material of the second substrate in a top down view, wherein the first landings overlie an exposed portion of the transparent substrate; and
second landings located on the second substrate.

15. The biochip of claim 14, wherein the first landings have a first density and the second landings have a second density different from the first density.

16. The biochip of claim 15, wherein the first landings and the second landings are different materials.

17. The biochip of claim 14, further comprising a flow meter.

18. The biochip of claim 14, further comprising a pressure transducer.

19. The biochip of claim 14, further comprising a heater.

20. The biochip of claim 14, further comprising a pump.

* * * * *